United States Patent
Hyman et al.

(10) Patent No.: US 7,668,586 B2
(45) Date of Patent: Feb. 23, 2010

(54) IN VIVO MULTIPHOTON DIAGNOSTIC DETECTION AND IMAGING OF A NEURODEGENERATIVE DISEASE

(75) Inventors: Bradley T. Hyman, Charlestown, MA (US); Richard Christie, New York, NY (US); Brian Bacskai, Charlestown, MA (US); Watt W. Webb, Ithaca, NY (US); Warren R. Zipfel, Ithaca, NY (US)

(73) Assignees: Cornell Research Foundation, Inc., Ithaca, NY (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 10/001,643

(22) Filed: Oct. 31, 2001

(65) Prior Publication Data
US 2003/0009104 A1     Jan. 9, 2003

Related U.S. Application Data

(60) Provisional application No. 60/245,306, filed on Nov. 2, 2000.

(51) Int. Cl.
*A61B 6/00* (2006.01)

(52) U.S. Cl. .................. 600/473; 600/476; 424/9.6; 356/300

(58) Field of Classification Search .............. 600/310, 600/473–477, 478, 407, 425, 431; 424/9.1, 424/9.6; 800/9; 435/4; 356/300
See application file for complete search history.

(56) References Cited

U.S. PATENT DOCUMENTS 4,576,173 A    3/1986   Parker et al.

(Continued)

FOREIGN PATENT DOCUMENTS

EP    0 512 965 A1    11/1992

(Continued)

OTHER PUBLICATIONS

Klunk WE, Bacskai B, Mathis C, Kaldasz S, McLellan M, Frosch M, Debnath M, Holt D, Wang Y, Hyman BT. Imaging Aβ Plaques in Living Transgenic Mice with Multiphoton Microscopy and Methoxy-X04, a Systemically Administered Congo Red Derivative. Jour Neuropathology and Experimental Neurology. Sep. 2002, vol. 61(9) pp. 797-805.*

(Continued)

*Primary Examiner*—Brian Casler
*Assistant Examiner*—Amanda Lauritzen
(74) *Attorney, Agent, or Firm*—Nixon Peabody LLP

(57) ABSTRACT

The present invention is directed to a method of detecting a neurodegenerative disease in a mammal by activating brain tissue of the mammal by application of radiation under conditions effective to promote a simultaneous multiphoton excitation of the brain tissue and to emit a fluorescence characteristic. The fluorescence characteristic is then compared to a standard fluorescence emitted by exciting healthy brain tissue of the mammal under the same conditions used to carry out the activating step. Brain tissue where the fluorescence characteristic differs from the standard fluorescence is identified as potentially having a neurodegenerative disease. Another aspect of the present invention is directed to a method of producing an image of brain tissue from a mammal by activating brain tissue of a mammal with radiation applied under conditions effective to promote a simultaneous multiphoton excitation of the brain tissue and to produce fluorescence. The fluorescence is then collected to produce an image of the brain tissue.

28 Claims, 26 Drawing Sheets

U.S. PATENT DOCUMENTS

| | | | |
|---|---|---|---|
| 4,592,361 A | 6/1986 | Parker et al. | |
| 4,895,156 A | 1/1990 | Schulze | |
| 5,034,613 A | 7/1991 | Denk et al. | |
| 5,062,428 A * | 11/1991 | Chance | 600/407 |
| 5,115,137 A | 5/1992 | Andersson-Engels et al. | |
| 5,119,815 A | 6/1992 | Chance | |
| 5,127,405 A | 7/1992 | Alcala et al. | |
| 5,197,470 A | 3/1993 | Helfer et al. | |
| 5,311,013 A | 5/1994 | Gutcheck et al. | |
| 5,323,775 A | 6/1994 | Joshi et al. | |
| 5,333,044 A | 7/1994 | Shaffer | |
| 5,341,805 A | 8/1994 | Stavridi et al. | |
| 5,353,790 A | 10/1994 | Jacques et al. | |
| 5,419,323 A | 5/1995 | Kittrell et al. | |
| 5,421,337 A | 6/1995 | Richards-Kortum et al. | |
| 5,579,773 A | 12/1996 | Vo-Dinh et al. | |
| 5,590,660 A | 1/1997 | MacAulay et al. | |
| 5,628,310 A | 5/1997 | Rao et al. | |
| 5,697,373 A | 12/1997 | Richards-Kortum et al. | |
| 5,699,795 A | 12/1997 | Richards-Kortum et al. | |
| 5,720,894 A | 2/1998 | Neev et al. | |
| 5,827,190 A | 10/1998 | Palcic et al. | |
| 5,986,271 A | 11/1999 | Lazarev et al. | |
| 6,070,096 A | 5/2000 | Hayashi | |
| 6,114,175 A * | 9/2000 | Klunk et al. | 436/63 |
| 6,166,385 A | 12/2000 | Webb et al. | |
| 6,178,041 B1 | 1/2001 | Simon | |
| 6,201,989 B1 | 3/2001 | Whitehead et al. | |
| 6,212,425 B1 | 4/2001 | Irion et al. | |
| 6,238,348 B1 | 5/2001 | Crowley et al. | |
| 6,280,386 B1 * | 8/2001 | Alfano et al. | 600/431 |
| 6,329,531 B1 * | 12/2001 | Turner et al. | 548/455 |
| 6,344,653 B1 | 2/2002 | Webb et al. | |
| 6,537,829 B1 * | 3/2003 | Zarling et al. | 436/514 |
| 6,600,947 B2 * | 7/2003 | Averback et al. | 600/476 |
| 6,818,218 B2 * | 11/2004 | Schenk | 424/185.1 |
| 7,107,092 B2 * | 9/2006 | Goldstein et al. | 600/476 |
| 7,183,105 B2 * | 2/2007 | Sabbadini et al. | 435/320.1 |
| 2002/0019023 A1 * | 2/2002 | Dasseux et al. | 435/40 |
| 2002/0115717 A1 * | 8/2002 | Gervais et al. | 514/553 |
| 2002/0127623 A1 * | 9/2002 | Minshull et al. | 435/7.92 |
| 2002/0133019 A1 * | 9/2002 | Klunk et al. | 548/156 |
| 2003/0236391 A1 * | 12/2003 | Klunk et al. | 534/11 |
| 2003/0236458 A1 * | 12/2003 | Hochman | 600/431 |
| 2004/0214774 A1 * | 10/2004 | Wisniewski et al. | 514/12 |
| 2005/0048539 A1 * | 3/2005 | Hyman et al. | 435/6 |
| 2005/0070538 A1 * | 3/2005 | Cheng et al. | 514/241 |
| 2005/0175626 A1 * | 8/2005 | Delacourte et al. | 424/185.1 |
| 2006/0034848 A1 * | 2/2006 | Kinoshita et al. | 424/146.1 |
| 2006/0039859 A1 * | 2/2006 | Sharma et al. | 424/1.49 |
| 2007/0042398 A1 * | 2/2007 | Peng et al. | 435/6 |

FOREIGN PATENT DOCUMENTS

| | | |
|---|---|---|
| EP | 0 920 831 A1 | 6/1999 |
| JP | 61-159936 | 7/1996 |
| WO | WO 93/25141 A1 | 12/1993 |
| WO | WO 94/22361 A1 | 10/1994 |
| WO | WO 95/29587 A1 | 11/1995 |
| WO | WO 96/10363 A1 | 4/1996 |
| WO | WO 98/22146 A2 | 5/1998 |
| WO | WO 99/65992 | 12/1999 |
| WO | WO 00/31588 | 6/2000 |

OTHER PUBLICATIONS

Christie et al., "Multiphoton Imaging of Alzheimer's Disease Neuropathology," *Society for Neuroscience Abstracts* 24(1-2):1219 (1998) (Abstract).

Christie et al., "In Vivo Multiphoton Imaging of Anyloid Deposition in Transgenic Mice," *Journal of Neuropathology and Experimental Neurology* 58(5):204 (1999) (Abstract).

Christie et al., "Multiphoton Imaging of Alzheimer's Disease Neuropathology," *Journal of Neuropathology and Experimental Neurology* 57:505 (#145) (1998) (Abstract).

Bacskai et al., "Chronic Imaging of Amyloid Plaques in the Live Mouse Brain Using Multiphoton Microscopy," *Proceedings of SPIE* 4262:125-133 (2001).

Christie et al., "Growth Arrest of Individual Senile Plaques in a Model of Alzheimer's Disease Observed by In Vivo Multiphoton Microscopy," *Journal of Neuroscience* 21(3):858-864 (2001).

Tromberg et al., "Optical Fiber Fluoroprobes for Biological Measurements," *Applied Spectroscopy* 38(1):38-42 (1984).

Dinkel et al., "Remote Two-Photon Excited Fluorescence Sensing in a Simulated Fermentation Broth," *Analytica Chimica Acta* 263:131-136 (1992).

Williams et al., "Mucosal Mast Cell Secretion Processes Imaged Using Three-Photon Microscopy of 5-Hydroxytryptamine Autofluorescence," *Biophysical Journal* 76:1835-1846 (1999).

Xu et al., "Multiphoton Excitation of Molecular Fluorophores and Nonlinear Laser Microscopy," in Lakowicz, ed., *Topics in Fluorescence Spectroscopy* vol. 5, New York, New York: Plenum Press, pp. 471-540 (1997).

Shear et al., "Multiphoton-Excited Visible Emission by Serotonin Solutions," *Photochemistry and Photobiology* 65(6):931-936 (1997).

Xu et al., "Multiphoton Excitation Cross-sections of Molecular Fluorophores," *Bioimaging* 4:198-207 (1996).

Maiti et al., "Measuring Serotonin Distribution in Live Cells with Three-Photon Excitation," *Science* 275:530-532 (1997).

Xu et al., "Multiphoton Fluorescence Excitation: New Spectral Windows for Biological Nonlinear Microscopy," *Proc. Natl. Acad. Sci. USA* 93:10763-10768 (1996).

Lago et al., "Two-Photon-Induced Fluorescence of Biological Markers Based on Optical Fibers," *Optics Letters* 20(20):2054-2056 (1995).

Williams et al., "Two-Photon Molecular Excitation Provides Intrinsic 3-Dimensional Resolution for Laser-based Microscopy and Microphotochemistry," *FASEB Journal* 8:804-813 (1994).

Denk et al., "Two-Photon Molecular Excitation in Laser-Scanning Microscopy," in Pawley, ed., *Handbook of Biological Confocal Microscopy*, New York, New York: Plenum Press, pp. 445-458 (1995).

Webb, "Non-Linear Laser Microscopy," *Progress in Biophysics & Molecular Biology*, XIIth International Biophysics Congress, 65:20 (1996) (Abstract).

Webb et al., "Multiphoton Fluorescence Correlation Spectroscopy with Single Molecules in Living Cells," 4th International Weber Symposium on Innovative Fluorescence Methodologies in Biochemistry and Medicine (1999) (Abstract).

Nichols et al., "Visualization of Mitochondria Via Two-Photon Microscopy of NADH: Indentifying Conditions that Maintain Cell Viability," *Biophysics Journal* 76:A9 (1999) (Abstract).

Nichols et al., "Identification of the Principle Sources of Two-Photon Autofluorescence From HeLa Cell Monolayers," *Biophysics Journal* 72:A346 (1997) (Abstract).

Williams et al., "Three-Photon Excitation Imaging of Serotonin Secretion by RBL-2H3 Cells," *Biophysics Journal* 72:A156 (1997) (Abstract).

Xu et al., "Multiphoton Excitation of Molecular Fluorophores and Native Biological Absorbers," *Biophysics Journal* 72:A90 (1997) (Abstract).

Shear et al., "Multiphoton-Excited Photochemistry Yields Visible Emission from Serotonin," *Biophysics Journal* 72:A346 (1997) (Abstract).

Xu et al., "Multiphoton Excitation of Fluorophores in Nonlinear Laser Microscopy," *OSA Annual Meeting/ILS-XII/Optics & Imaging in the Information Age Advance Program* p. 158 (1996) (Abstract).

Webb, "Biological Applications of Nonlinear Laser Microscopy," *Advanced Solid-State Lasers*, Twelfth Topical Meeting, p. 65 (1997) (Abstract).

Webb et al., "Multiphoton Molecular Excitation to Illuminate Non-Linear Laser Microscopy," in Barbara et al., eds., *Springer Series in Chemical Physics: Ultrafast Phenomena X*, vol. 62, Berlin: Springer-Verlag, p. 133 (1996) (Abstract).

Webb, "Non-Linear Optical Microscopy," *Biophysics Journal* 70:A429 (1996) (Abstract).

Webb, "Non-Linear Laser Microscopy," *Photochemistry and Photobiology* 63:45S (1996) (Abstract).

Xu et al., "Three-Photon Excited Fluorescence and Applications in Nonlinear Laser Scanning Microscopy," *Biophysics Journal* 70:A429 (1996) (Abstract).

Maiti et al., "Multiphoton Fluorescence Spectroscopy Through Optical Fibers," *Biophysics Journal* 72:A217 (1997) (Abstract).

Masters et al., "Confocal Microscopy and Multi-Photon Excitation Microscopy of Human Skin In Vivo," *Optics Express* 8(1):2-10 (2001).

Masters et al., "Multiphoton Excitation Microscopy of Human Skin In Vivo: Early Development of an Optical Biopsy," *In SFM99* (Saratov Fall Meeting 99), Saratov State University Optics Department, Russia (1999).

Helmchen et al., "A Miniaturized Two-Photon Fiber-Scanning Microscope for In Vivo Imaging," *Society for Neuroscience* vol. 25:Abstract 322.1 (1999) (abstract).

Glanzmann et al., "Time-Resolved Spectrofluorometer for Clinical Tissue Characterization During Endoscopy," *Review of Scientific Instruments* 70(10):4067-4077 (1999).

Arendt et al., "Investigation of Early Cancerous Changes in Bladder Tissue by Autofluorescence," Proceedings—19th International Conference—*IEEE/EMBS* pp. 2290-2293 (1997).

Zonios et al., "Morphological Model of Human Colon Tissue Fluorescence," *IEEE Transactions on Biomedical Engineering* 43(2):113-122 (1996).

\* cited by examiner

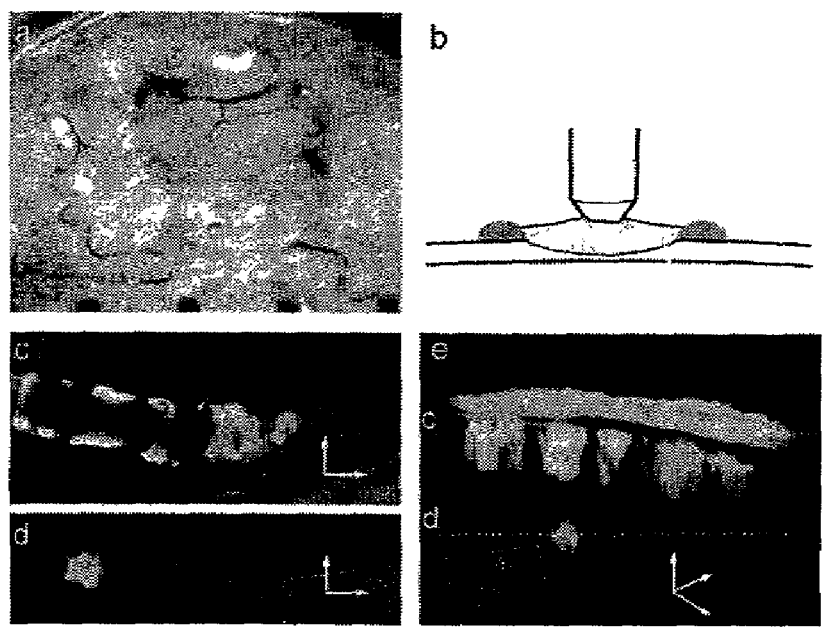
FIGURES 2A-E

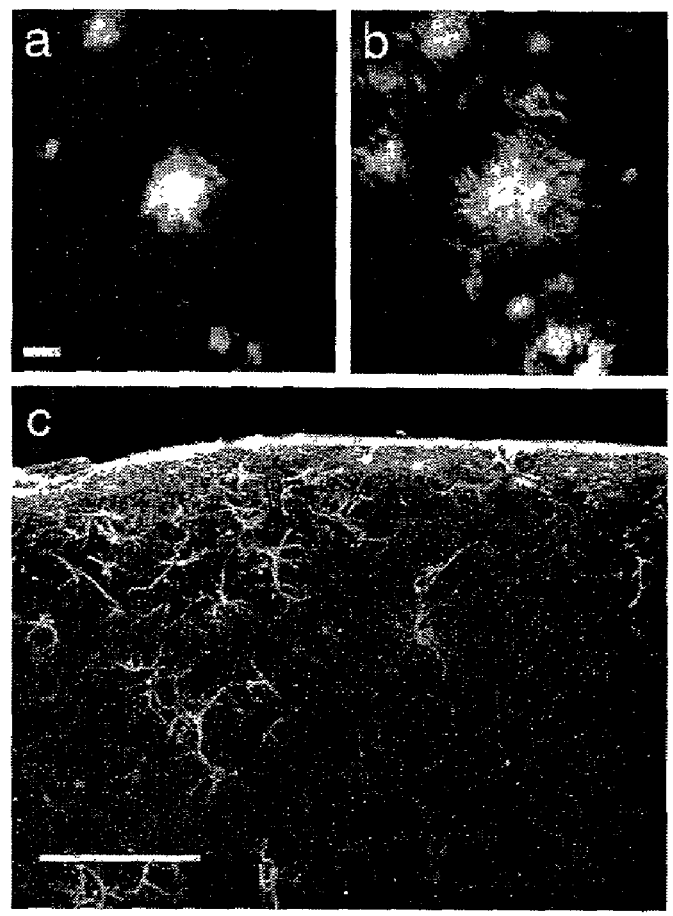
FIGURES 3A-C

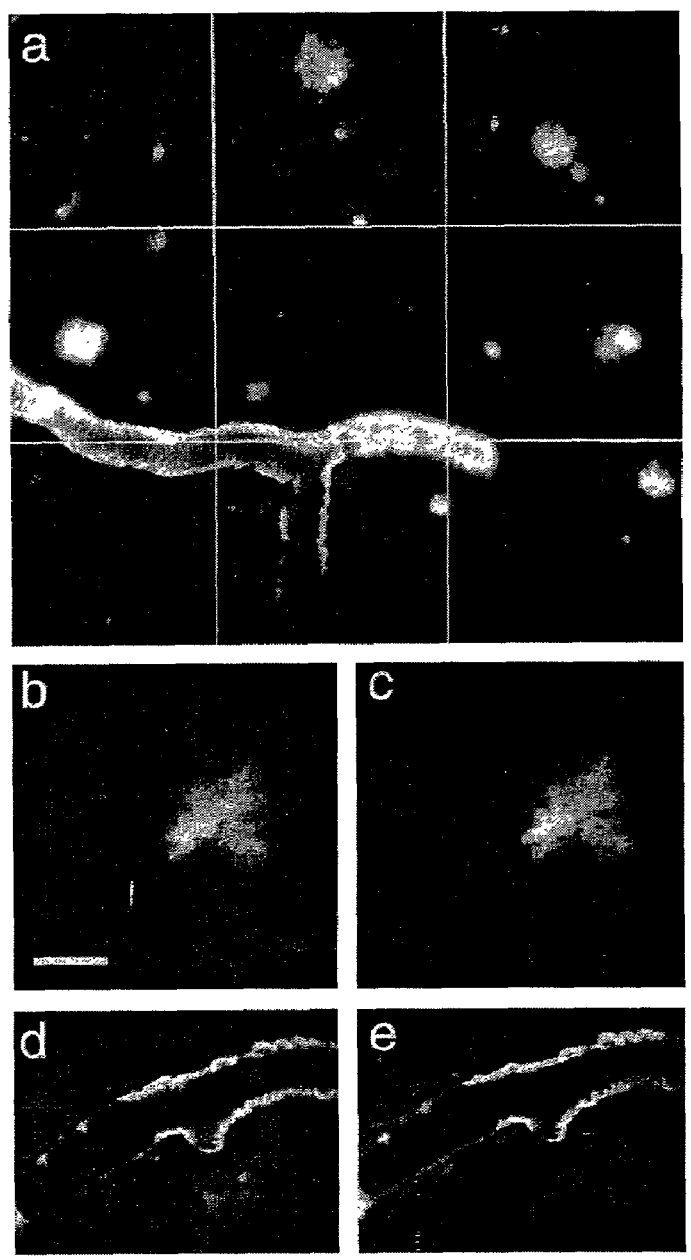
FIGURES 4A-E

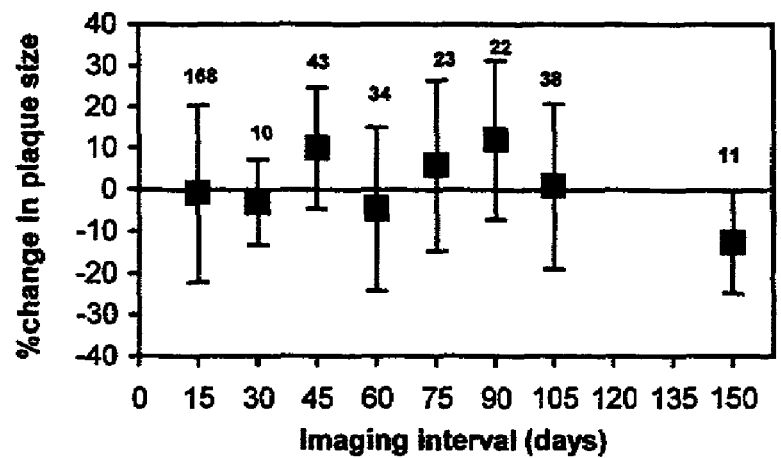
A
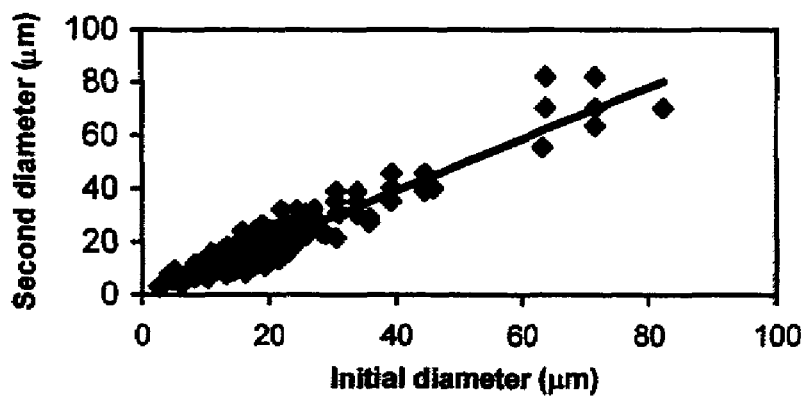
B
FIGURES 5A-B

FIGURES 7A-B

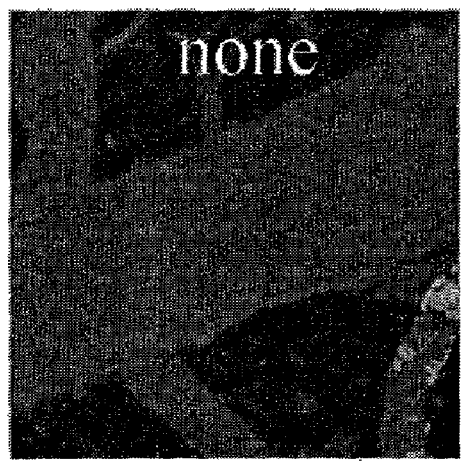 
 
FIGURE 9

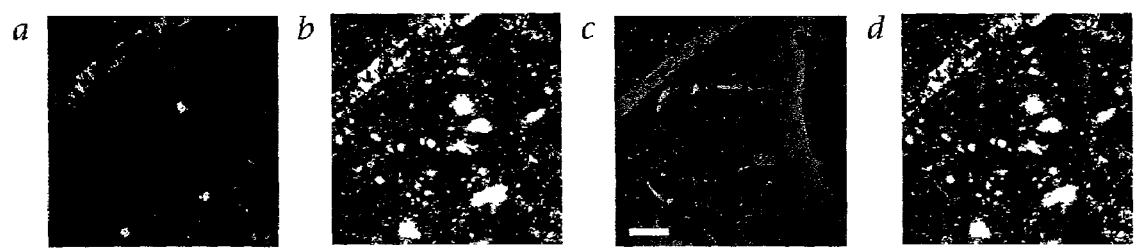
FIGURES 19A-D

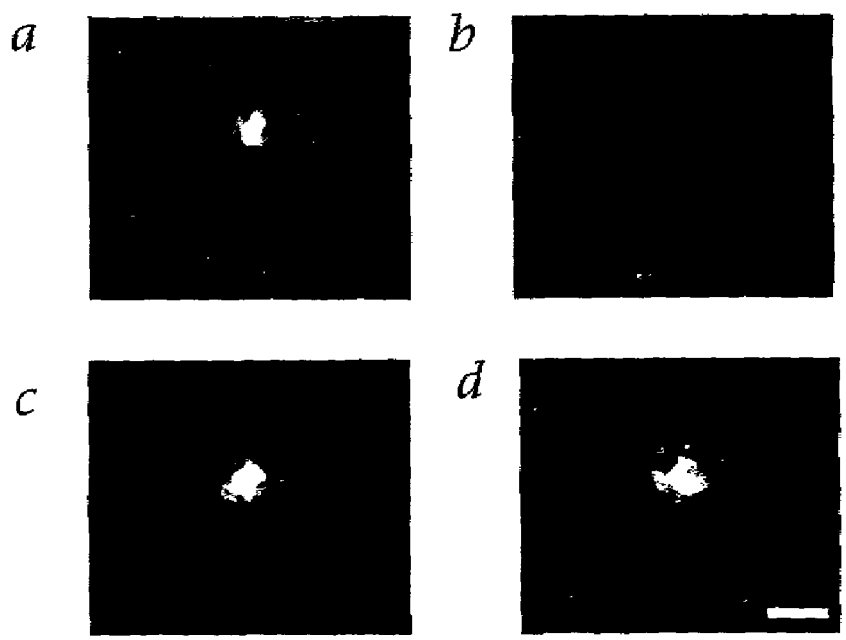
FIGURES 20A-D

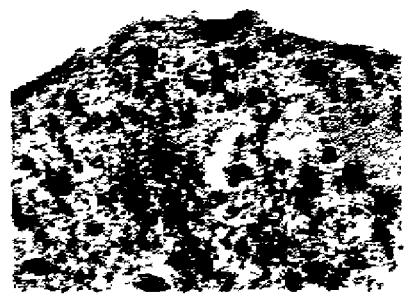
FIGURES 21A-B

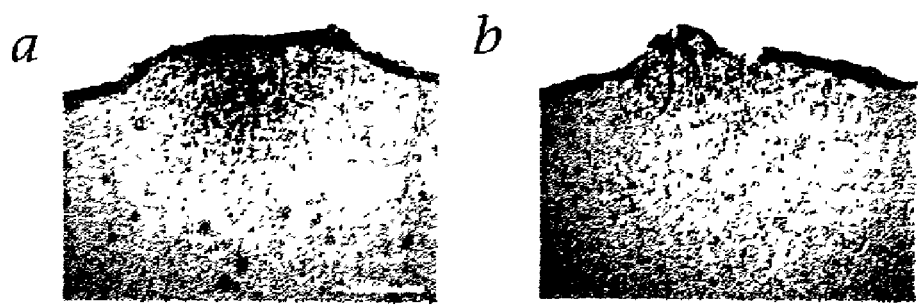
FIGURES 22-A-B

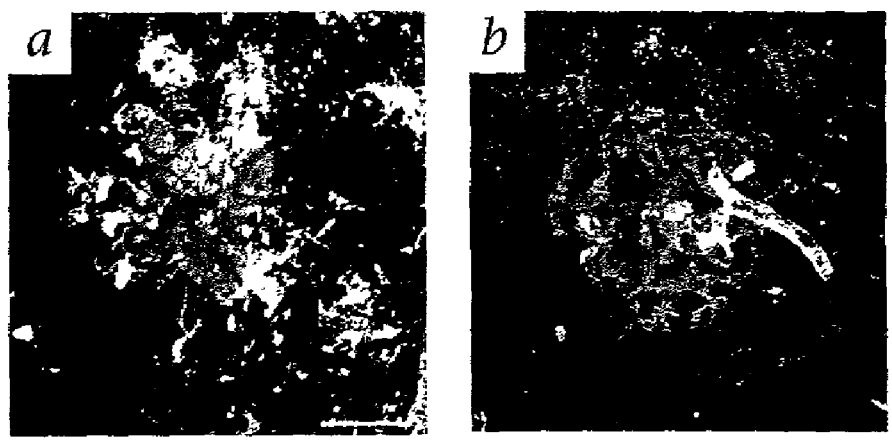
FIGURES 23A-B

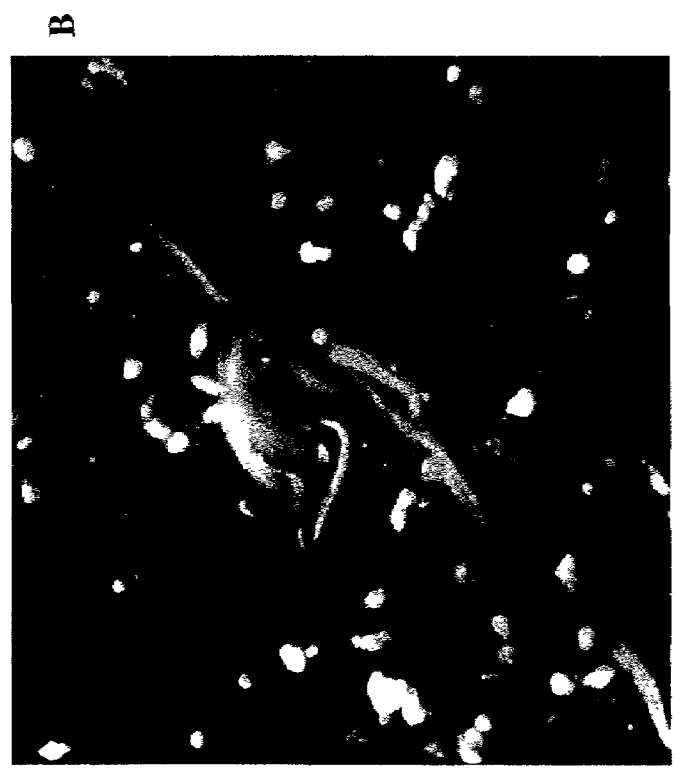
FIGURES 24A-B

IN VIVO MULTIPHOTON DIAGNOSTIC DETECTION AND IMAGING OF A NEURODEGENERATIVE DISEASE

This application claims benefit of U.S. Provisional Patent Application Ser. No. 60/245,306, filed on Nov. 2, 2000.

This invention was developed with government funding under National Institutes of Health Grant Nos. AG08487 and RR04224. The U.S. Government may have certain rights.

FIELD OF THE INVENTION

The present invention relates to the in vivo multiphoton diagnostic detection and imaging of a neurodegenerative disease.

BACKGROUND OF THE INVENTION

Alzheimer's Disease is a devastating illness affecting nearly 4 million Americans, costing the country billions of dollars in direct care, lost income, and—most importantly—costing untold anguish for millions of American families.

The disease symptoms start insidiously, with relatively non-specific signs and symptoms. Subtle memory loss, occasional word-finding difficulties, irritability and aggressiveness can all be signs of a disease process from a clinical perspective, that has already affected the brain substantially. Over the course of several years, the disease progresses to profound amnesia to the point where patients do not know themselves, or their family. Frequently this amnesia is accompanied by frustration and paranoia. Ultimately patients lose all ability to care for themselves—to dress themselves, to bathe, even to control their bowel and bladder. Their last years are frequently spent in a nursing home. As the average age of the population grows, the number of Alzheimer patients will explode because it is a strongly age-related illness.

While these clinical symptoms are going on, the changes in the brain are marked. By the time the very first clinical symptoms appear, there are innumerable microscopic deposits of a protein called amyloid ("A-beta" or "Aβ"), as well as changes in the brain cells themselves. As the disease progresses, the brain shrinks and losses as many as 50% of its cells.

Genetic risk factor analysis and molecular biology suggest strongly that it is the depositon of Aβ that is the critical aspect of this disease process. Seeing Aβ and neuronal change, neurofibrillary tangles, in the brain under the microscope provides a definitive diagnosis to a neuropathologist. However, these changes are far too small (100 times too small) to be seen by even the most sophisticated clinical imaging devices such as computerized tomography or magnetic resonance imaging.

The ability to detect amyloid deposition and neurofibrillary changes in neurons in vivo would provide a definitive diagnostic test for Alzheimer's Disease, and compares to quite non-specific clinical symptoms at the beginning of the disease process. Moreover, the ability to visualize and quantitate these changes would provide a definitive means of tracking progression of disease, and effectiveness of potential therapeutics.

The present invention is directed to overcoming the deficiencies in the prior art by providing a method of diagnostically detecting and imaging Alzheimer's Disease and other neurodegenerative diseases.

SUMMARY OF THE INVENTION

The present invention is directed to a method of detecting a neurodegenerative disease in a mammal by activating brain tissue of the mammal by application of radiation under conditions effective to promote a simultaneous multiphoton excitation of the brain tissue and to emit a fluorescence characteristic. The fluorescence characteristic is then compared to a standard fluorescence emitted by exciting healthy brain tissue of the mammal under the same conditions used to carry out the activating step. Brain tissue where the fluorescence characteristic differs from the standard fluorescence is identified as potentially having a neurodegenerative disease.

Another aspect of the present invention is directed to a method of producing an image of brain tissue from a mammal by activating brain tissue of a mammal with radiation applied under conditions effective to promote a simultaneous multiphoton excitation of the brain tissue and to produce fluorescence. The fluorescence is then collected to produce an image of the brain tissue.

The current state of the art is that diagnosis of Alzheimer's Disease occurs only after clinical manifestations of marked memory loss and other cognitive impairments occur. Neuropathological studies suggest that the disease process actually starts many years prior to these overt symptoms. An imaging technology that allows detection of the pathological process prior to clinical symptoms would allow treatments aimed at prevention of progression rather than simply treatment of symptoms. Ideally, a biomarker of this nature can be used for presymptomatic identification of patients, as a method of following the efficacy of therapy, and as a method to direct different therapies. Each of these applications would provide a substantial advance over the current state of affairs.

BRIEF DESCRIPTION OF THE DRAWINGS

FIG. 1A illustrates the manner in which a patient's skull is imaged. In FIG. 1B, imaging is carried out with a spectroscopic system. FIG. 1C illustrates imaging with a single mode optical fiber and terminal lens.

FIGS. 2A-E show the preparation of a skull for in vivo imaging. FIG. 2A shows the gross appearance of skull through dissecting microscope prior to imaging. The pial vasculature is visible through the intact but thinned region of skull. Anterior and midline sutures are also visible in the image. Scale marks are spaced 1 mm apart. FIG. 2B is a schematic diagram of the microscope objective during imaging. The thinned area of skull is bathed in a pool of artificial cerebrospinal fluid (light gray), retained by a ring of bone wax (dark gray). A small break is made in the lateral wall of the thinned area to allow for thioflavine S entry. FIG. 2C is the in vivo visualization of thioflavine S-positive ("ThioS") amyloid in a 15-month old Tg2576 mouse. Single optical section near the surface of the skull. Thioflavine S-positive amyloid angiopathy is visible ringing the pial arteriole in this image. The fainter autofluorescence of the skull bone is visible in the lower right corner, and the fibrous autofluorescence of the dura is visible as a band at lower right. FIG. 2D shows another optical section from the same z-series as in FIG. 2C, but 50 µm deeper into the brain, showing a thioflavine S-positive amyloid deposit in layer 1 of the mouse cortex. FIG. 2E shows the perpendicular volume rendering of the entire stack of images, with the skull visible at the top, the amyloid-encrusted pial vessel just beneath, and the thioflavine S-positive plaque deep in the living brain. The autofluorescent dura can also be seen as a faint layer between the vessel and the skull. The approximate levels of optical sections shown in FIGS. 2C and 2D are represented by dotted lines. The scale bars in FIGS. 2C-E are 25 µm.

FIGS. 3A-C confirm the thioflavine S-positive structures were indeed senile plaques. This was demonstrated by applying thioflavine S and an anti-amyloid-beta monoclonal antibody, cy3-labeled 10D5 (Elan Pharmaceuticals, South San Francisco, Calif.), to the surface of a fixed but intact Tg2576 brain. In FIG. 3A, the fluorescence emission in the range 380-480 nm shows Thioflavine S staining the amyloid core of a plaque about 40 μm deep into the brain. In FIG. 3B, emission in the 560-650 nm range shows the Cy3-10 D5 staining of the same Aβ surrounding the thioflavine S positive core. Scale bar=10 μm. FIG. 3C shows glial fibrillary acidic protein immunoreactivity in a section through the area imaged by multiphoton microscopy 2 days previously. Sparse immunoreactive astrocytes, not substantially different from adjacent (non-imaged) cortex, suggest minimal tissue response to imaging. Scale=100 μm.

FIGS. 4A-E show the in vivo imaging of thioflavine S positive amyloid deposition in a Tg2576 mouse. FIG. 4A is a 3×3 montage of 60× fields acquired on initial imaging day. Optical sections were obtained every 2 micrometers for a distance of 200 micrometers from the inner surface of the skull; images were aligned in the x, y, and z axes, then projected onto a single image revealing amyloid angiopathy and senile plaques. Scale bar=100 μm. FIG. 4B shows the in vivo imaging of a thioflavine S-positive plaque approximately 40 μm deep to the skull surface. This image is a single optical section through the body of the plaque. Scale bar=10 μm. FIG. 4C shows the same plaque as in FIG. 4B, reimaged two days later under identical imaging conditions. FIG. 4D is a single optical section showing thioflavine S-positive amyloid angiopathy associated with a pial arteriole. Scale bar=20 μm. FIG. 4E shows the same arteriole imaged in FIG. 4D after two days.

FIGS. 5A-B show the analysis of variability of plaque measurements. In FIG. 5A, the percent change (average +/− standard deviation) for all plaque measurements binned into 0.5-month groups shows no trend in either the average measure or the variability of measurement over the time interval examined. N's for each measurement are noted above the standard deviation bars. FIG. 5B is a linear regression plot of initial measurement and subsequent measurement for all time intervals, showing tight correlation for all plaque sizes. The slope of the line approaches unity (0.98) with a correlation coefficient ($R^2$=0.89).

FIG. 7A is a volume rendering of a set of 3 plaques during an initial imaging session. FIG. 7B is a volume rendering of the same region, imaged 64 days later, showing the initial plaques joined by a novel thioflavine S-positive plaque. The fibrous autofluorescence at lower left is dura mater. Scale bar=50 μm.

FIG. 9 shows examples of the co-occurrence of amyloid angiopathy and microvascular anatomy. A semiquantitative rating scale (none, mild, moderate, severe) was employed as illustrated in this figure.

*=$p<0.01$.

Figure 12:
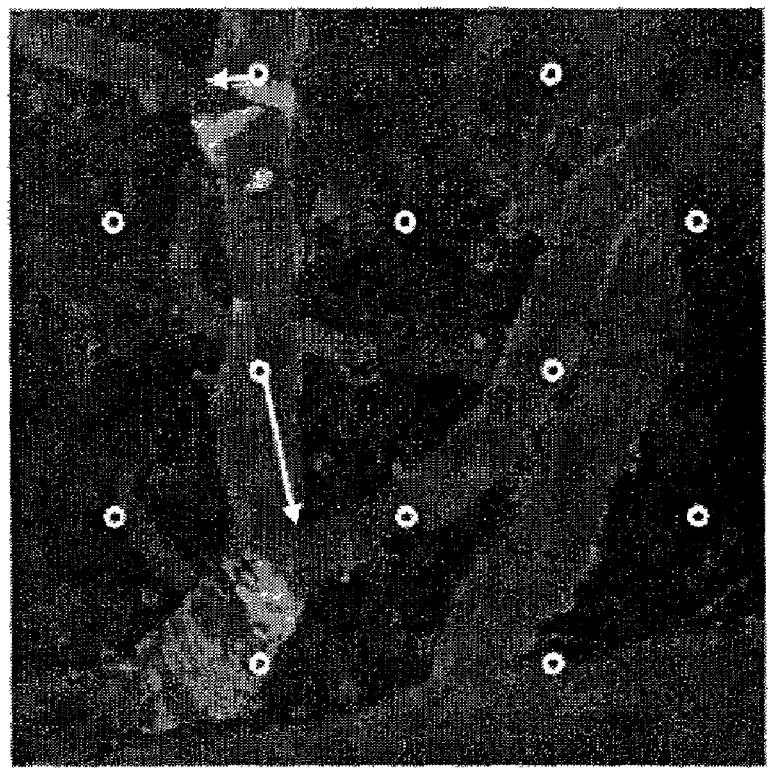

FIG. 12 shows an example of mild amyloid angiopathy occurring near the branch points of vesssels. The method for measuring distance is illustrated with an overlay of random points from which the distance from the nearest branch point is measured.

Figure 13:
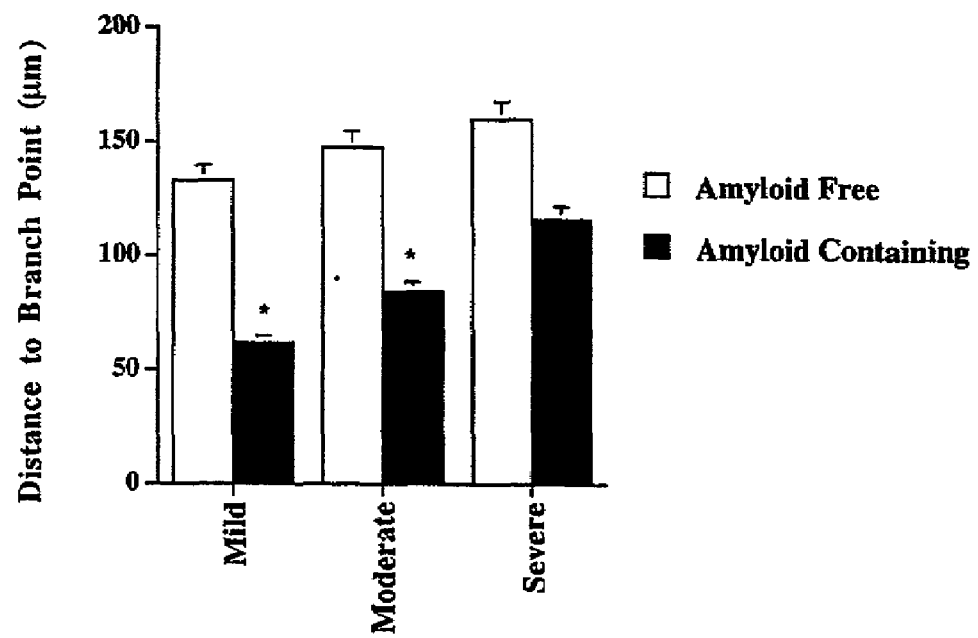

FIG. 13 shows the distance af amyloid deposits from nearest branch point. Measurements were carried out as described with reference to FIG. 12. The significant differences were seen in both mild (n=75 vessel segments, $p<0.005$) and moderate (n=73 vessel segments, $p<0.005$) vessels, with amyloid tending to occur near branch points. A smaller difference, not reaching statistical significance was seen in severely affected vessels (n=59).

Figure 14:
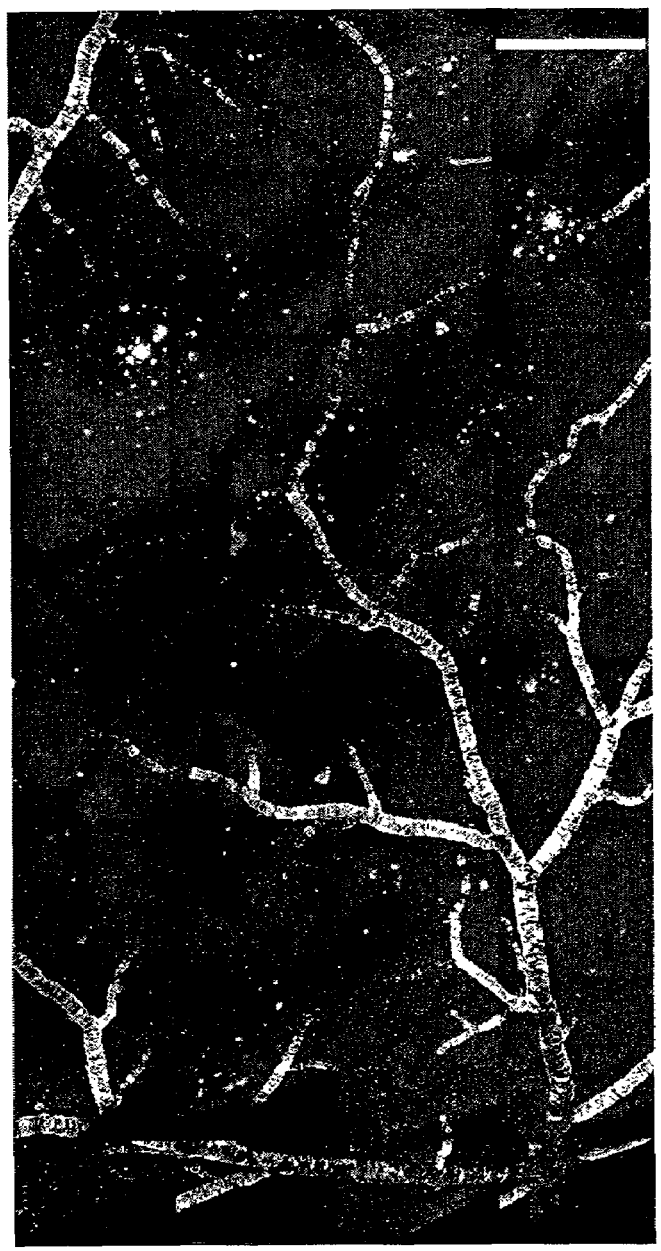

FIG. 14 shows the thioS positive amyloid angiopathy in the Tg2576 mouse. The intact fixed brain of a 16 month old Tg2576 mouse was stained with thioS (0.005%) and imaged using two-photon excitation at 750 nm. This image is a montage of 4×8 z-series collected with a 20× objective. The midline of the brain is at the top of the figure, and the brain was oriented with the anterior pole to the left. Extreme curvature at the lateral edge of the brain interfered with montage generation, distorting the lowermost portion of the image. The middle cerebral artery emerges from behind the lateral edge of the brain on the right, and courses towards the midline. ThioS positive vessel-associated amyloid, as well as superficial parenchymal thioS-positive plaques are clearly visible. Surface venules are seen as negatively stained background profiles. Scale bar(upper right)=600 μm.

FIGS. 15A-B shows that the overexpression of mutant amyloid precursor protein ("APP") does not disrupt smooth muscle cells independent of amyloid deposition. Phalloidin-labeled smooth muscle cells in young (6 month) Tg2576 animals are arranged neatly around the circumference of the vessel, with no apparent space between adjacent cells. FIG. 15A shows the phalloidin-stained smooth muscle cells in a pial vessel from a Tg− animal. FIG. 15B shows smooth muscle cells in a pial vessel of a Tg+ animal. Scale bar=20 μm.

FIGS. 16A-F show the effect of amyloid deposition on smooth muscle cells in 14 month old and 22 month old Tg2567 animals. FIG. 16A shows phalloidin-labeled smooth muscle cells in the wall of a pial arteriole in a 14 month old Tg2576 animal. FIG. 16B shows thioS-positive amyloid surrounding the vessels. Smooth muscle cells are clearly disrupted in areas of amyloid deposition as compared to unaffected regions of the same vessel. Smooth muscle cells surrounded by amyloid are disorganized and isolated, though there is no apparent loss of cells along the length of the vessel. FIG. 16D shows smooth muscle cell staining in a 24 month old Tg2576 animal. FIG. 16E shows thioS-positive amyloid surrounding the vessel. At this age, overt loss of smooth muscle cells along the length of the vessel is evident, along with disruption of remaining cells. Regions of the vessel unaffected by amyloid, however, retain normal smooth muscle cell organization. (See FIG. 16C and F). Superimposed color images showing both phalliodin and thio S staining. Scale bar=20 μm.

Figure 17:
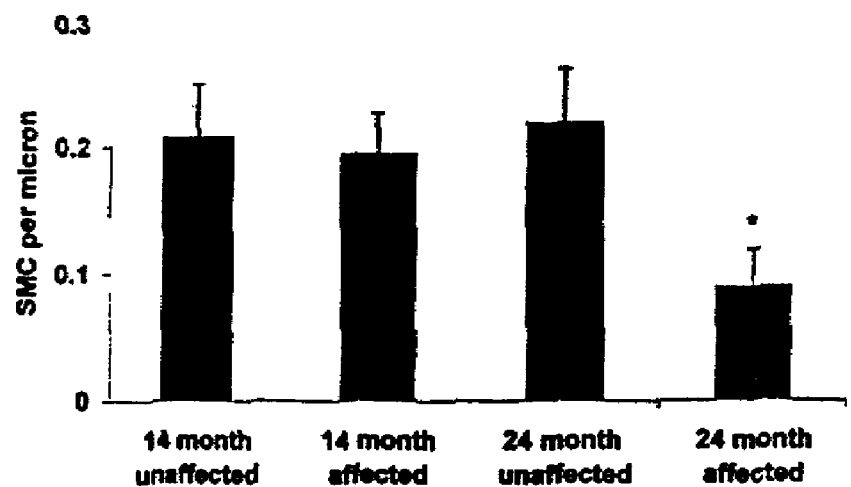

FIG. 17 shows the quantitation of smooth muscle cell density in amyloid-laden versus amyloid-free vessels in 14 mo and 24 mo Tg2576 mice. Smooth muscle cell linear density was measured as described. Density was measured in affected and unaffected vessels from both age groups. The 24 month old amyloid-laden set of vessels has significantly smaller smooth muscle cell density ($p<0.01$, ANOVA) than either the amyloid-free vessels from the same animal or amyloid-free vessels from younger transgenic and non-transgenic animals.

Figure 18:
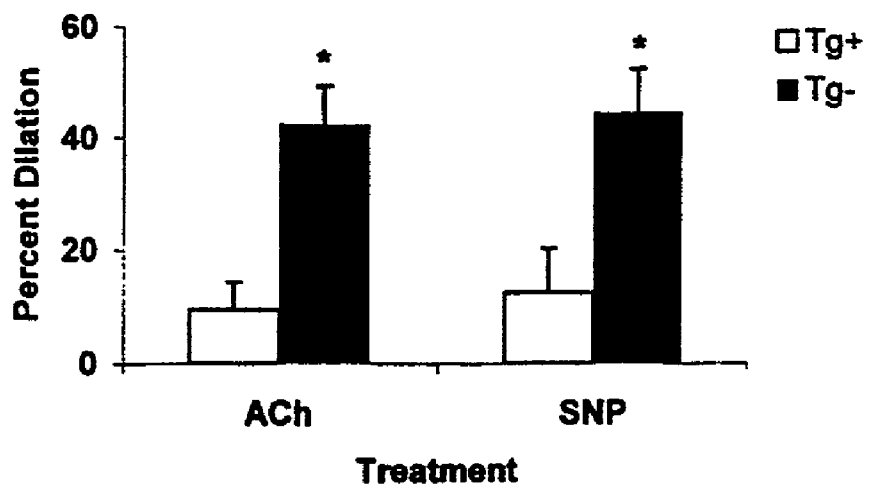

FIG. 18 shows the response of pial vessels to ACh and SNP. Maximal percent dilation in response to ACh ($10^{-6}$M) and SNP ($0.5 \times 10^{-6}$M) in 14 month old Tg+ (n=4 of 5, one outlier excluded) and Tg− (n=3 of 3) mice. Bars are mean +/− SD. *, $p<0.05$ by ANOVA.

FIGS. 19A-D show the in vivo imaging of amyloid-β deposits in 20 month old homozygous PDAPP mice. Reconstructions of stacks of Z series images taken at 5 micron steps with a 20× objective (FIGS. 19A-B) and 2 micron steps with a 60× objective (FIGS. 19C-D) starting from just below the cortical surface to approximately 150 microns below the surface. Amyloid-β is visualized with a dilute solution of fluorescein labeled monoclonal antibody 10D5. (FIGS. 19A and C) Initial imaging session shows numerous 10D5 immunoreactive amyloid-β plaques in the neuropil and associated with vessels in one representative animal (FIGS. 19B and D). Three days later exactly the same sites were re-imaged with fluorescein10D5. Surprisingly, very little of the neuropil amyloid-β remains, directly showing reversal of previously existing amyloid-β deposits. Note that the vessel associated amyloid-β is not clearly altered. Magnification bar=50 μm in FIGS. 19A and B, 25 μm in FIGS. 19C and D.

FIGS. 20A-D ascertain whether the apparent clearance of amyloid-β was due to application of an anti-amyloid β antibody or to the surgical preparation, imaging, and other non-specific factors by replacing 10D5 in the first imaging session with 16B5, a monoclonal antibody directed against human tau that does not cross react with rodent tau (Sobey et al., "Effect of Nitric Oxide and Potassium Channel Agonists and Inhibitors on Basilar Artery Diameter," Am J Physiol 72:H256-H262 (1997), which is hereby incorporated by reference), and used thioflavine S as the imaging agent. FIGS. 20A and 20B, respectively, show a thioflavine S positive plaque in the first imaging session and 3 days after application of 10D5. FIG. 20C depicts a thioflavine S positive plaque in a 16B5 treated animal does not change 3 days later (FIG. 20D). Magnification bar=20 μm.

FIGS. 21A-B show the histological analysis of imaged brains from 20 mo. old homozygous PDAPP mice using directly labeled antibody 3D6, showing an extraordinarily high level of amyloid-β deposits throughout the cortex and hippocampal formation. There was a marked diminution of amyloid-β staining at the site of 10D5 application. FIG. 21A depicts the immunostaining with biotinylated 3D6, an anti-amyloid-β monoclonal antibody that has a distinct epitope (aa 1-5) compared to 10D5 (aa 3-6), which shows a 100-200 micron deep area that was essentially devoid of diffuse amyloid-β deposits, in contrast to the intense deposits found in adjacent sections or medial or lateral to the site. FIG. 21B shows that there were no changes in 3D6 immunoreactive amyloid-β plaques observed after initial treatment with 16B5 application. Magnification bar=200 μm.

FIGS. 22A-B show that marked local microglial activation, as assessed with biotin labeled tomato lectin (Sigma Chemical Co., St. Louis, Mo.), occurred three days after skull preparation and imaging in both (FIG. 22A) the 10D5 and (FIG. 22B) the 16B5 groups. Magnification bar=200 μm.

FIGS. 23A-B show confocal thin optical sections (0.2 micron) that were reconstructed to illustrate the intimate relationship of microglia with remaining amyloid-β three days after treatment with 10D5-fluorescein. FIG. 23A depicts luorescein labeled tomato lectin, which detects microglia, and biotin labeled 3D6 detected with Cy3 avidin, which detects amyloid-β. A marked microglial response surrounding remaining amyloid-β plaques was deserved. As indicated in FIG. 23B, distal to the site, for example in temporal lobe, the association of microglia with amyloid-β is much more modest. Magnification bar=20 μm.

FIG. 24A shows the autofluorescence of neurofibrillary tangles and lipofusion droplets from post-mortem brain tissue in a human Alzheimer's Disease patient. FIG. 24B shows the fluorescence of neurofibrillary tangles from post-mortem brain tissue in a human Alzheimer's Disease patient using an antibody against the tau protein; this demonstrates the fluorescence in FIG. 24A is attributable to the tau protein.

DETAILED DESCRIPTION OF THE INVENTION

The present invention is directed to a method of detecting a neurodegenerative disease in a mammal by activating brain tissue of the mammal by application of radiation under conditions effective to promote a simultaneous multiphoton excitation of the brain tissue and to emit a fluorescence characteristic. The fluorescence characteristic is then compared to a standard fluorescence emitted by exciting healthy brain tissue of the mammal under the same conditions used to carry out the activating step. Brain tissue where the fluorescence characteristic differs from the standard fluorescence is identified as potentially having a neurodegenerative disease.

Another aspect of the present invention is directed to a method of producing an image of brain tissue from a mammal by activating brain tissue of a mammal with radiation applied under conditions effective to promote a simultaneous multiphoton excitation of the brain tissue and to produce fluorescence. The fluorescence is then collected to produce an image of the brain tissue.

Figure 1A:
FIGS. 1A-C show different embodiments for imaging neurodegenerative disease in accordance with the present invention.
Figure 1B:
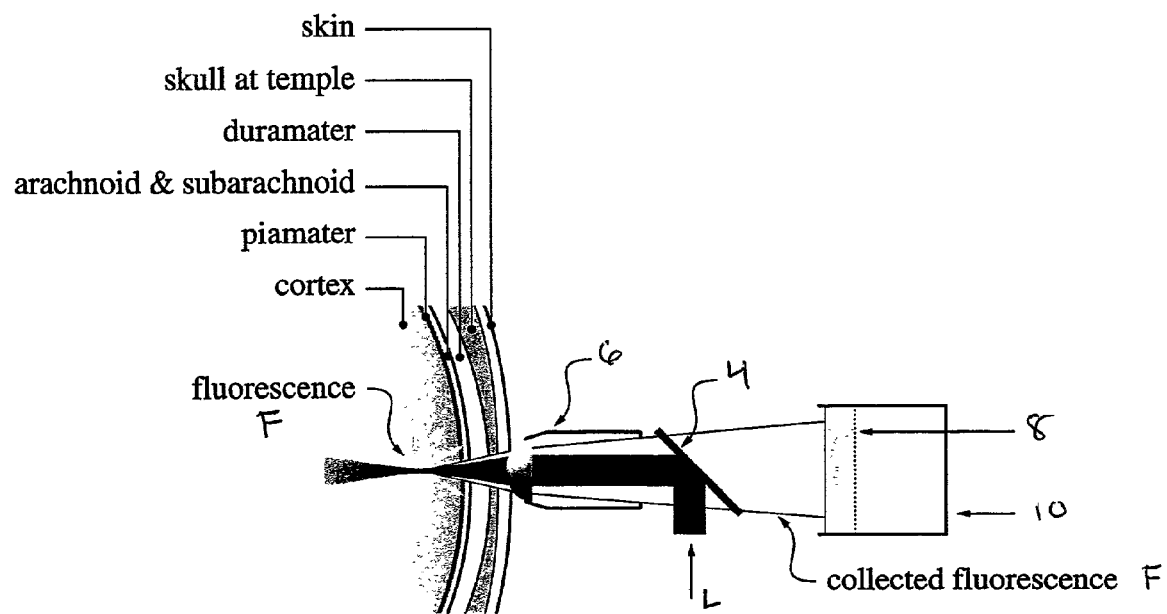
Figure 1C:
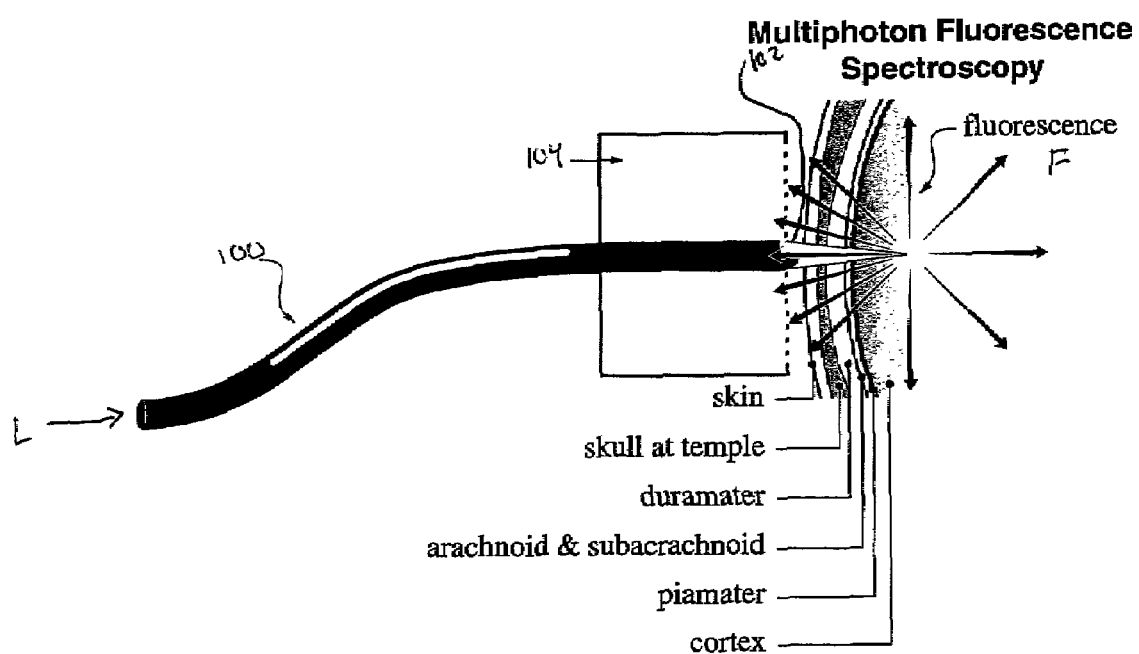

FIGS. 1A-C show different embodiments for imaging neurodegenerative disease in a patient in accordance with the present invention.

FIG. 1A illustrates how a patient P's skull is imaged by placing imaging device 2 against the skull.

FIG. 1B carries out imaging with a spectroscopic system. This system includes dichroic mirror 4, lens 6, spectroscopic selection device 8, and photo-detector 10. In use, multiphoton radiation L from a laser is directed against dichroic mirror 4 which redirects this radiation through lens 6. Lens 6 is placed against a thin part of the skull of patient P so that multiphoton radiation L is passed through the patient's skin, skull, duramater, arachnoid and subarachnoid, and piamater and into the cortex. Within the cortex, radiation L causes fluorescence F to occur and this fluorescence passes through lens 6, past dichroic mirror 4, and to spectroscopic selection device 8 which is provided with photodetector 10. Photodetector 10 receives fluorescence F passed to it by spectroscopic selection device 8 and causes an image to be created. This image is then examined for the purpose of diagnosing Alzheimer's Disease or other neurodegenerative diseases.

FIG. 1C shows a second embodiment for carrying out the method of the present invention. In this version of the present invention, single mode optical fiber 100, terminal lens 102, and detector 104 are used to carry out the imaging procedure of the present invention. In use, multiphoton radiation L is passed through the patient's skin, skull, duramater, arachnoid and subarachnoid, and piamater and into the cortex or some or all of these layers need to be penetrated to allow penetration of the fiber closer to the cortex surface. Within the cortex, radiation L causes fluorescence F to occur and this fluorescence passes into detector 104 where an image is created. This image is then examined for the purpose of diagnosing Alzheimer's Disease or other neurodegenerative disease.

As shown in FIGS. 1B-C, the diagnostic/imaging procedure of the present invention can be carried out non-invasively by applying radiation L to the patient's head. Alternatively, the patient's skull can be thinned by drilling or abrading the skull. Alternatively, the brain can be exposed by surgically opening the skull and then subjection the brain to radiation L.

Detection of the multiphoton excited fluorescence and the second and third harmonic of the laser excitation generated in tissue can be accomplished through an optical fiber that provides the excitation and, of course, through surrounding fibers in a bundle or through thick optical tubes for efficient collection of light excited near the tip of the single mode excitation fiber or fibers. There is a significant advantage in fluorescence collection efficiency for multiphoton tissue fluorescence over single photon excitation, because the emission is localized near the fiber tip where it is most accessible to collection optics. Desirably, the present invention is carried out with a plurality of optical fibers, including a single excitation fiber surrounded by a plurality of collection fibers.

Effective multiphoton molecular excitation is made possible, in accordance with the present invention, by the combination of (a) the very high, local, instantaneous intensity and (b) the temporal concentration of a pulsed laser. A high intensity, long wavelength, monochromatic light source which is focusable to the diffraction limit such as a titanium sapphire mode locked solid state laser, with each pulse having a duration of about 100 femtoseconds ($100\times10^{-15}$ seconds) at a repetition rate of about 80 MHz. Other lasers that are also effective for multiphoton excitation and harmonic generation can also be used. Because of the high instantaneous power provided by the very short duration intense pulses focused to the diffraction limit, there is an appreciable probability that a fluorophore (a fluorescent dye), contained in the target, and normally excitable by a single high energy photon having a short wavelength, typically ultraviolet, will absorb two long wavelength photons from the laser source simultaneously. This absorption combines the energy of the two photons in the fluorophore molecule, thereby raising the fluorophore to its excited state. When the fluorophore returns to its normal state, it emits light, and this light then passes to a suitable detector.

The multiphoton excitation of fluorophores by highly intense, short pulses of light constitutes a general fluorescence microscopy technique for imaging which provides improved background discrimination and reduces photobleaching of the fluorophores. This is because the focused illumination provided in the microscope fills a converging cone as it passes into the specimen. All of the light which reaches the plane of focus at the apex of the converging cone, except the tiny fraction which is absorbed in the fluorophore, then passes out the opposite side of the specimen through a diverging cone. Only in the region of the focal point on the object plane at the waist formed by the converging and diverging cones is the intensity sufficiently high to produce multiphoton absorption in the specimen fluorophore, and this intensity dependence enables long wavelength excitation only in the small local volume of the specimen surrounding the focal point. This absorption is produced by means of a stream of fast, high intensity, femtosecond pulses of relatively long wavelength which retains a moderate average illumination intensity of long wavelength light throughout the remainder of the specimen outside the region of the focal point. As a result, photobleaching of the fluorophore outside the plane of focus is virtually eliminated. One-photon absorption of the long wavelength light is negligible, and outside the plane of focus the instantaneous intensity is too low for appreciable two-photon absorption and excitation, even though the time average illumination is in reality nearly uniform throughout the depth of the specimen. This effect also significantly reduces the damage to living cells.

In order to obtain three dimensional resolution, the present invention can utilize two-photon excitation of a fluorophore which has a one-photon absorption peak at a wavelength which overlaps or exceeds one-half that of the exciting light. For three-photon excitation, the one-photon absorption overlaps one-third that of the exciting light. To accomplish this, the laser produces a very short pulsed laser beam of high instantaneous power and of a relatively long wavelength, for example in the visible red of the infrared range. This light is directed to a specimen containing a fluorophore normally excited by a single photon having a short wavelength (e.g., ultraviolet radiation) range so that two low energy (red) photons must combine their energy to provide the same excitation of the specimen that would be provided by a single high energy (ultraviolet) photon. Both the excitation and hence the fluorescence rates in the specimen are proportional to the square of the intensity of the incident light. In the focused excitation laser beam, the intensity of the long wavelength incident light becomes high enough to excite the fluorophores in the specimen only in the region of the focal point. This focal point may be adjustably positioned within the specimen so that fluorescence and/or photolysis of the specimen are produced only in a selected ellipsoidal volume around the focus. Thus, in accordance with the present invention, only long wavelength excitation light has to pass through the specimen, and this long wavelength light is focused to produce sufficient intensity to excite fluorescence only in a very small region. This fluorescence is produced even if the fluorophore normally absorbs only in the ultraviolet. Since the focal point can be selectively positioned in the specimen, three-dimensional resolution is provided in both scanning fluorescence microscopy and in photolysis, including photolysis of photon-activatable reagents which can be released by photolysis.

In accordance with the present invention, the necessary excitation intensity is provided from a radiation light source which may be, for example, a titanium sapphire mode locked laser generating pulses of light having a wavelength in the red region of the spectrum, for example about 700-1000 nm, or with the pulses having a width of $10^{-9}$ seconds to $10^{-15}$ seconds, conveniently at about 80 MHz repetition rate. Other bright pulsed lasers may also be used to produce light at different relatively long wavelengths in the infrared or visible red region of the spectrum, for example, to generate the necessary excitation photon energies which will add up to the appropriate absorption energy band required by the fluorophores in the spectrum which normally would be excited by absorption of a single photon in the spectral region having wavelengths about one-half the wavelength of the incident light. If shorter excitation wavelengths are needed, the laser wavelengths can be divided by 2, 3, or 4 by external harmonic generation. Thus, for example, two photons in the visible red region at 750 nm would combine to excite a fluorophore which normally absorbs light in the ultraviolet region at or above 375 nm, while two photons in the infrared region of, for example, 1070 nm, would excite a fluorophore which absorbs at or above 535 nm in the visible light region.

In a modified form of the invention, the single wavelength light source can be replaced by two different long wavelength laser sources so that the incident light beam consists of two superimposed pulsed light beams of high instantaneous power and of different wavelengths. The wavelengths of the incident beam are selected to excite a fluorophore which is absorbent at a short wavelength which may be described as:

$$1/\lambda_{abs}=1/\lambda_1+1\lambda_2$$

where $\lambda_{abs}$ is the short wavelength of the absorber, and $\lambda_1$ and $\lambda_2$ are the laser incident beam wavelengths.

In two-photon excitation, with a typical two-photon cross section δ of:

$$\delta=10^{-58} m^4 s/photon$$

with the pulse parameters given above (100 fsec. pulses at a repetition rate of 80 MHz), and with the beam focused by a lens of numerical aperture A—1.4, the average incident laser power ($P_0$) of approximately 50 mW saturates the fluorescence output of a fluorophore at the limit of one absorbed photon per pulse per fluorophore. The number $n_\alpha$ of photons absorbed per fluorophore per pulse depends on the following relationship:

$$n_a \approx \frac{P_o^2 \delta}{\tau f^2}\left[\frac{A^2}{2hc\lambda}\right]^2$$

where
  τ is the pulse duration;
  f is the repetition rate;
  $P_0$ is the average incident laser power;
  δ is the photon absorption cross section;
  h is the Planck quantum of action;
  c is the speed of light; and
  A is the numerical aperture of the focusing lens.

The fluorescence emission could be increased, however, by increasing the pulse repetition frequency up to the inverse fluorescence lifetime, which typically is:

$$\tau_f^{-1}=10^9 S^{-1}$$

For comparison, one-photon fluorescence saturation occurs at incident powers of about 3 mW.

In addition to measurement of intrinsic tissue fluorescence (also known as autofluorescence) with multiphoton excitation, it is possible to utilize photoactive agents, including fluorescent dyes, in conjunction with multiphoton microscopy to image properties of cells and tissues. Suitable photoactive agents include dyes which are excited by multiphoton excitation such as, organic molecules whose fluorescence changes when they bind metal ions such as $Ca^{2+}$, $Mg^{2+}$, $Na^+$ or $K^+$ or $H^+$, including dyes like DAPI (4',6-diamidino-2-phenylindole, dihydrochloride). Many such dyes are suitable for application in vivo. Such photoactive agents fluoresce upon binding to lesions of a neurodegenerative disease or other neuroanomalies. In carrying out the first embodiment of the present invention, the standard fluorescence is determined prior to treating the brain tissue with at least one photo-active agent.

The multiphoton imaging technique of the present invention can be used to observe plaques and neurons in the brains of living mammals. In addition, tangles can also be observed.

There are several possible approaches to observing the tangles and plaques: tangles are made up highly structured aggregation of tau protein, which under an electron microscope adopt a confirmation called perihelical filaments. It has been discovered that this protein confirmation is autofluorescent using wavelengths utilized for multiphoton microscopy (approximately 700 nanometer excitation, emission approximately 450 nanometer). This observation would allow detection of neurofibrillary tangles in the brain, either through imaging using devices designed to provide scanning capabilities or through spectroscopy, in which an atomic resolution is lost but the unique biochemical signature of protein structure can still be detected. The autofluorescence due to tangles can be discriminated from other brain structures due to the unique wavelength properties that have been discovered for the tangle protein, as well as ultimately using other techniques such as fluorescence lifetime imaging to discriminate from the low-level autofluorescence in the background. Thus, one could envision applying the long wavelength light through the skull to the brain substance and measuring the emitted autofluorescence. The long wavelength light passes readily through the soft tissue and overlying bone in systems currently in use to measure hemoglobin saturation in the brain, suggesting the feasibility of this approach.

A separate approach will be taken for amyloid deposition. To date, amyloid does not appear to be autofluorescent so that to visualize the amyloid, a contrast agent needs to be applied. It has been found that a commonly used reagent, thioflavine S, can be applied directly to the cortical surface or into the spinal fluid. This dye is intensely fluorescent only when bound to amyloid plaques. Thus, in another embodiment of the invention, thioflavine S or a dye with similar amyloid-binding properties could be given to patients either introduced into the spinal fluid or, using compounds that cross the blood brain barrier, systemically injected, and the brain subsequently imaged using long wavelength light. Again, either spectroscopy or direct imaging would allow for the detection and quantitation of the amount of amyloid present. Such a technique, in which long wavelength near infrared light is used to generate fluorescent markers of neurofibrillary change or amyloid deposition could be utilized for diagnosis as well as to determine the amount of these changes present in the brain, providing a quanitative readout for therapeutic interventions.

In addition to diagnosing/imaging Alzheimer's Disease, the present can also be used diagnose/image other neurodegenerative diseases. Examples of such diseases include Parkinson's Disease, Huntington's Disease, and Lou Gehrig's Disease.

EXAMPLES

Example 1

In vivo Imaging of Amyloid Deposition

Nine male Tg2576 mice (mean age 18.6 months (Hsiao, et al., "Correlative Memory Deficits, Aβ Elevation, and Amyloid Plaques in Transgenic Mice," *Science,* 274:99-102

(1996), which is hereby incorporated by reference in its entirety), were used for the in vivo imaging of plaques. These mice express human amyloid precursor precursor carrying the Swedish mutation under the hamster prion protein promoter. The skull was prepared 2-6 days prior to imaging. Mice were anesthetized with Avertin (Tribromoethanol, 250 mg/kg IP). A high-speed drill (Fine Science Tools, Foster City Calif.) was used to thin the skull in a circular region, approximately 1-1.2 mm in diameter (FIG. 2A), using a dissecting microscope for gross visualization of the site. Heat and vibration artifacts were minimized during drilling by frequent application of artificial cerebrospinal fluid ("ACSF"; 125 mM NaCl; 26 mM $NaHCO_3$; 1.25 mM $NaH_2PO_4$; 2.5 mM KCl; 1 mM $MgCl_2$; 1 mM $CaCl_2$; 25 mM glucose). Skull thickness was repeatedly assessed with a surgical probe (Roboz, Rockville Md.), and drilling stopped when the bone displayed flexibility in a central region approximately 0.6 mm in diameter. Clear visualization of pial vasculature was an additional indication of skull thinness. The scalp was then sutured, and the animal allowed to recover. On the day of imaging, the animal was re-anesthetized, the scalp reflected, and the small amount of connective tissue that had grown in the interim was removed by scraping. The tip of a 22 gauge needle was used to make a small break in the lateral wall of the skull preparation in order to facilitate thioflavine S diffusion into the brain. Thioflavine S (0.005% in ACSF, Sigma Chemical, St. Louis Mo.) was then applied for 20 minutes to the site. A small ring of molten bone wax was applied to the skull surrounding the site, and this well was filled with ACSF to create an aqueous reservoir for the long working distance, water immersion dipping objectives (Olympus, Tokyo, Japan). The thin skull preparation also eliminates the need for application of a coverslip (Svoboda, et al., "In Vivo Dendritic Calcium Dynamics in Neocortical Pyramidal Neurons," *Nature*, 385:161-165 (1997), which is hereby incorporated by reference in its entirety) to the imaging site, as preservation of this thin layer of bone is sufficient to stabilize the cardiac and respiratory motion of the brain inherent in in vivo imaging. The animal was immobilized in custom-built stage-mounted ear bars and a nosepiece, similar in design to a stereotaxic apparatus. The thin skull site was then placed directly under the objective lens of the microscope (Olympus BX-50) for imaging (FIG. 2B).

Two photon fluorescence was generated with 750 nm excitation from a mode-locked Ti:Sapphire laser (Tsunami, Spectra Physics, Mountain View Calif.; 5.45W Millenium V pump laser (Spectra Physics), power at back aperture of objective 10 mW, pulse 60-100 fs) mounted on a commercially available multiphoton imaging system (BioRad 1024ES, BioRad, Hercules Calif.). External detectors containing three photomultiplier tubes (Hamamatsu Photonics, Bridgewater N.J.) collected emitted light in the range of 380-480 nm, 500-540 nm, and 560-650 nm; all thioflavine S figures are from the 380-480 nm channel. Imaging was performed using the normal scan speed of the scanhead, dwell time=1.5 µs per pixel. Up to four thin skull preparations were made per animal in order to maximize the number of plaques available for measurement. Thioflavine S (0.005% in ACSF) was applied to the preparation at each imaging session. The site was first imaged with a 10× objective (1230 mm square field; NA=0.5), to map the surface of the thin skull preparation and to facilitate repositioning of the site during subsequent imaging sessions. X-Y stage encoders (Boeckeler, Tucson Ariz.) were calibrated with their origin at the center of the thin skull site, and were used to preserve the relative coordinates of higher-magnification images within the site. Nine z-series using a 60× objective (205×205 µm; NA=0.8) were then collected in a 3×3 array covering the thinnest portion of the site, by moving the stage exactly 205 µm in the X or Y direction. The incremental z-step was 2 µm, and the series was collected from the skull surface to a depth of about 150 µm into the brain. The starting position of the z-axis motor relative to skull position was recorded for later z-axis alignment during montage generation. Following completion of image collection, the animal was removed from the stage, the ring of bone wax removed, the skull washed with sterile saline, and the scalp sutured. The animal was warmed to 37° C. during recovery from anesthesia. Total time of anesthesia was limited to 2 hours.

Example 2

Image Analysis

Montages were reconstructed into a single stack of images using Scion Image (Scion Corp, Frederick Md.). The area of individual plaque cross-sections was measured in each optical section by thresholding at two standard deviations above the mean of an adjacent background region. Plaques that did not satisfy criteria of imaging were eliminated from the measurement set. Plaques on the edge of the imaging area or on one of the montage lines were rejected due to the potential imprecision of moving the animal on the stage. Plaques whose intensity was not sufficiently above background for appropriate thresholding were also eliminated. This rejected many plaques, typically deep in the preparation, that appeared to be present, but were too faint to measure using the automatic threshold technique. Finally, plaques whose images contained any appreciable motion artifact were rejected. Maximal plaque diameter was then calculated from the cross-section of largest area for each plaque. Volume rendering was performed using VoxBlast (VayTek, Fairfield Iowa) on a Windows NT based workstation (Precision 610, Dell Computer, Round Rock Tex.).

Example 3

Angiography

The tail of the animal was warmed on a heating pad to dilate the blood vessels, and approximately 0.05 ml fluorescein (25 mg/ml) in sterile PBS was injected into a tail vein of the mouse at least 20 minutes prior to imaging. The dye did not cross the blood-brain barrier and permitted concurrent visualization of blood vessels throughout the imaging volume in the brain.

Example 4

Cross Sectional Histology

Two groups of animals (n=3 per group; mean ages 12.6 months and 22.6 months) were used for the histological measurement of amyloid deposition, measuring amyloid burden and size distribution as previously described (Hyman, et al., "The Lack of Accumulation of Senile Plaques or Amyloid Burden in Alzheimer's Disease Suggests a Dynamic Balance Between Amyloid Deposition and Resolution," *J. Neuropathol Exp. Neurol.*, 52:594-600 (1993), which is hereby incorporated by reference in its entirety). Images of thioflavine S stained sections were collected using two-photon excitation with 750 nm light. All fields of the cortex containing thioflavine S-positive amyloid deposits were imaged in a given section, until approximately 80 plaques were imaged per animal. Images were then transferred to Scion Image, (Scion Corp), where a threshold was applied, the image was filtered slightly to remove noise, and plaques were automatically outlined by the software's particle analysis protocol. Images were manually edited to remove thioflavine S-positive blood vessels and edge-effect artifacts. Sections containing few Thioflavine S-positive plaques were exhaustively sampled, counting all plaques within this cortical area. Random systematic sampling of about 10 fields per section was applied to those sections containing heavier amyloid burdens, and a 400 μm×400 μm counting frame was used with automatic selection and measurement to count thioflavine S-positive plaques. Plaques were counted in three sections per animal in this way; the adequacy of the sampling strategy was reflected in coefficients of error of 10% or less. Results were expressed as the density of thioflavine S-positive plaques per square millimeter. Statistical significance of the observed difference in plaque number between the groups was assessed by t-test.

Multiphoton microscopy was adapted for these studies, because it has unique advantages for in vivo imaging, and its resolution is on the order of one micrometer (Denk, et al., "Two-Photon Laser Scanning Fluorescence Microscopy," *Science*, 248:73-76 (1990), which is hereby incorporated by reference in its entirety). Since only acute in vivo imaging has been reported to date in any system, a new approach for long-term repeat imaging was developed. A thin, transparent bone window about 1 mm in diameter and about 20 micrometers thick is formed with a high-speed burr in the skull of an anesthetized Tg2576 mouse (FIG. 2A). A small break is made in the lateral wall of the site to allow for delivery of fluorophore to the brain, but the bone remains otherwise intact within the thinned region. An upright Olympus BX-50 fixed stage microscope containing a modified stage insert was used for in vivo imaging (FIG. 2B).

Thioflavine S is a standard amyloid-binding fluorophore that excites in the ultraviolet range and has an emission maximum of around 450 nm. It has been extensively used to label amyloid deposits in human Alzheimer's Disease tissue (Kelenyi, "Thioflavin S Fluorescent and Congo Red Anisotropic Stainings in the Histologic Demonstration of Amyloid," *Acta Neuropathol (Berl)*, 7:336-348 (1967), which is hereby incorporated by reference in its entirety) as well as in transgenic mouse models of amyloid deposition. It is among the stains recommended by the Consortium to Establish a Registry for Alzheimer's Disease (CERAD) for the neuropathological diagnosis of Alzheimer's Disease in post-mortem tissue (Mirra, et al., "The Consortium to Establish a Registry for Alzheimer's Disease (CERAD). Part II. Standardization of the Neuropathologic Assessment of Alzheimer's Disease," *Neurology*, 41:479-486 (1991), which is hereby incorporated by reference in its entirety). A dilute solution of thioflavine S was applied to the brain of a living 18 month old Tg2576 transgenic mouse for in vivo visualization of amyloid deposits using multiphoton microscopy. Thin optical sections were obtained every 2.0 micrometers from the bone window surface to approximately 150 micrometers deep to the surface, using 750 nm light for 2-photon excitation of the fluorophore. Reconstruction of these thin optical sections revealed thioflavine S-positive amyloid surrounding pial arterioles with the classic segmental appearance of amyloid angiopathy (Vonsattel, et al., "Cerebral Amyloid Angiopathy Without and With Cerebral Hemorrhages: A Comparative Histological Study," *Ann. Neurol.*, 30:637-649 (1991), which is hereby incorporated by reference in its entirety) in superficial sections (FIG. 2C). Deeper optical sections (FIG. 2D) revealed parenchymal thioflavine S-positive amyloid plaques. Plaques were visualized in this way up to 150 μm deep to the surface of the cortex.

The imaged plaques share the morphology of classic thioflavine S-positive senile plaques seen in tissue from transgenic animals and from Alzheimer's Disease cases, and no such structures were seen in non-transgenic control littermates. That these structures are indeed senile plaques was further confirmed by incubation of the postmortem fixed brain from the transgenic mouse with a fluorescently labeled antibody to Aβ (10D5, Elan Pharmaceuticals (Hyman, et al., "Kunitz Protease Inhibitor-Containing Amyloid Beta Protein Precursor Immunoreactivity in Alzheimer's Disease," *J. Neuropathol Exp. Neurol.*, 51:76-83 (1992), which is hereby incorporated by reference in its entirety) directly labeled with Cy3 (Amersham, Piscataway, N.J.). This double stain revealed colocalization of thioflavine S with surrounding amyloid-β immunoreactivity (FIGS. 3A-B). As expected, thioflavine S stains plaques with a dense core, which are a subset of all Aβ immunoreactive structures (Schmidt, et al., "Chemical and Immunological Heterogeneity of Fibrillar Amyloid in Plaques of Alzheimer's Disease and Down's Syndrome Brains Revealed by Confocal Microscopy," *Am. J. Pathol.*, 147:503-515 (1995), which is hereby incorporated by reference in its entirety). Moreover, histologic analysis two to seven days following such imaging reveals no overt damage, neuronal loss, or increase in reactive astrocytes (FIG. 3C) as assessed by glial fibrillary acidic protein staining, suggesting that the thin-skull preparation and imaging protocol are well-tolerated by the living brain.

The potential of multiphoton microscopy for non-destructive in vivo imaging opens the possibility of repeated visualization of plaques over time within a living animal. FIG. 4A is an example of the imaging approach in a live mouse. The skull was prepared, thioflavine S was applied, and a three by three matrix of a 615 μm×615 μm region of the site was imaged using a 60× water immersion objective. Upon recovery from anesthesia, the animal was returned to its cage where it showed no sign of impairment or discomfort following imaging. Representative images from one animal collected at an interval of two days are shown in FIGS. 4B-E. An example of a plaque (FIG. 4B) and amyloid angiopathy (FIG. 4D) are shown at the initial imaging session. Two days later, the animal was re-anesthetized and thioflavine S was reapplied to the thinned region of the skull. Imaging was carried out under identical conditions as at the initial session. Both plaques (FIG. 4C) and amyloid angiopathy (FIG. 4E) were clearly revisualized after two days, and appear to have been unaltered since the initial imaging session.

In order to study the natural history of thioflavine S positive amyloid deposits, plaques in five additional animals (mean age 18.6 months) were imaged over progressively longer time periods. A total of 41 imaging sessions yielded 29 data sets containing plaques that were successfully imaged at more than one time, which contained 349 aligned pairs of plaques over time intervals ranging from 2 to 150 days. As many as 5 separate imaging sessions of the same volume were obtained in each animal. Qualitatively, the structure and size of the vast majority of plaques remain remarkably stable over these extended periods of observation. Fine details of the morphology of individual plaques are recognizable in subsequent images obtained months later, including finger-like appendages, and small clusters of thioflavine S positive amyloid (e.g. FIGS. 4B-C).

Quantitative analysis of plaque diameter over time, measured in the optical section with the greatest diameter, confirms this qualitative judgment. Analysis of changes in plaque diameter for the entire set of measurements is presented in FIG. 5. Taken as a population, the amount of variability in the two measures is essentially the same regardless if the measures were obtained 4 days or 150 days apart (FIG. 5B). The initial measurement of the size of an individual plaque is an excellent predictor of a subsequent measurement of that same plaque, whether over an interval of days or months. The slope of the linear regression graph plotting size of a plaque at initial imaging to its size at a later time, taking all measurements for periods over an interval of 2 days to 150 days was nearly unity (slope=0.98; $R^2$=0.89). These data are consistent with plaques being extraordinarily stable in vivo objects over an extended period of time.

Figure 6:
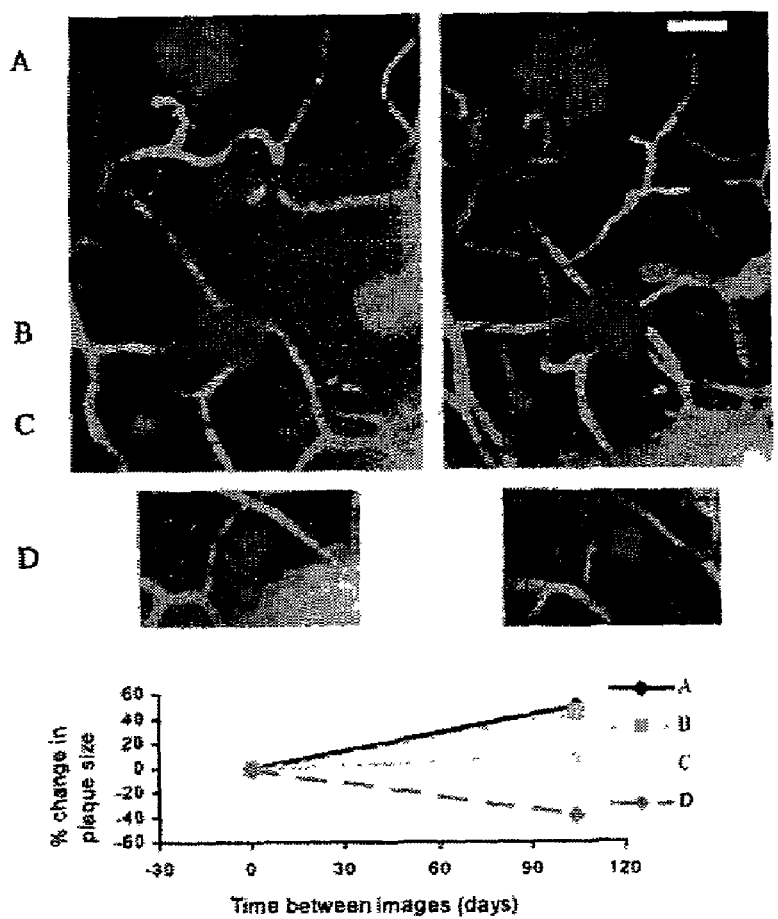
FIG. 6 shows a subpopulation of plaques change size over time. The images are 2-channel volume rendered stacks of thioflavine S plaques (red) and fluorescein angiograms (green) taken from the same animal at the initial imaging session (left images) and 104 days later (right images). Four clearly imaged plaques can be seen in these volumes, labeled A-D. The autofluorescence of the dura appears at the upper edge of the volume stacks, and appears slightly different in the images here and in FIG. 7, because the image stacks are not exactly coincident at their initial depth. The graph below represents the percent change in diameter for each plaque. The plaques labeled A and B increase in size by about 50%, plaque C remains the same size, and plaque D decreases by 40%. Scale bar=20 μm.

However, close examination of the data sets reveals a small number of plaques that appear to have either grown or shrunk substantially between imaging sessions. There was concern that this apparent change could be due to technical factors and so systematically applied working criteria to eliminate known potential sources of measurement error. For example, data from plaques that fell on the border of one of the 205 μm×205 μm fields comprising the montage was rejected, or if the plaque was the deepest plaque imaged in a given session. In several animals, fluorescein angiography was performed at the same time as thioflavine S imaging, in order to create additional internal landmarks to facilitate lining up the plaques from one imaging session to another. After carefully evaluating over three hundred pairs of plaques, only 14 clear examples of marked growth or resolution (i.e. a change in size by 40%) were found. FIG. 6 shows examples of plaques from a volume rendered stack of images of the same region of cortex, obtained 104 days apart, showing the same four plaques (in red) as well as the fluorescein angiogram (green). Qualitative and quantitative analyses show that two of the plaques have grown substantially (about 50%), one has become substantially smaller (by over 40%), and one has not changed size at all. These data show that, within the same region and during the same imaging sessions, some plaques appear to grow while others shrink. Technical issues such as thioflavine S concentration or power at the focal plane cannot account for some getting larger and others smaller within a region as small as a single 3 dimensional field, so that the most parsimonious explanation is that, in these instances, plaque size is changing.

Figure 7:
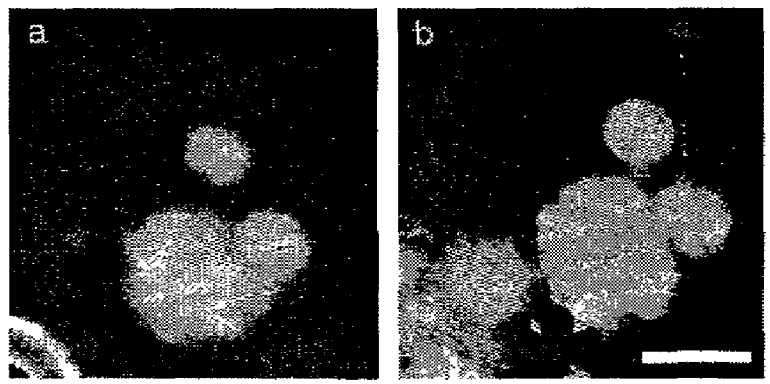
FIGS. 7A-B show the appearance of a novel plaque in the imaged region.
Figure 8:
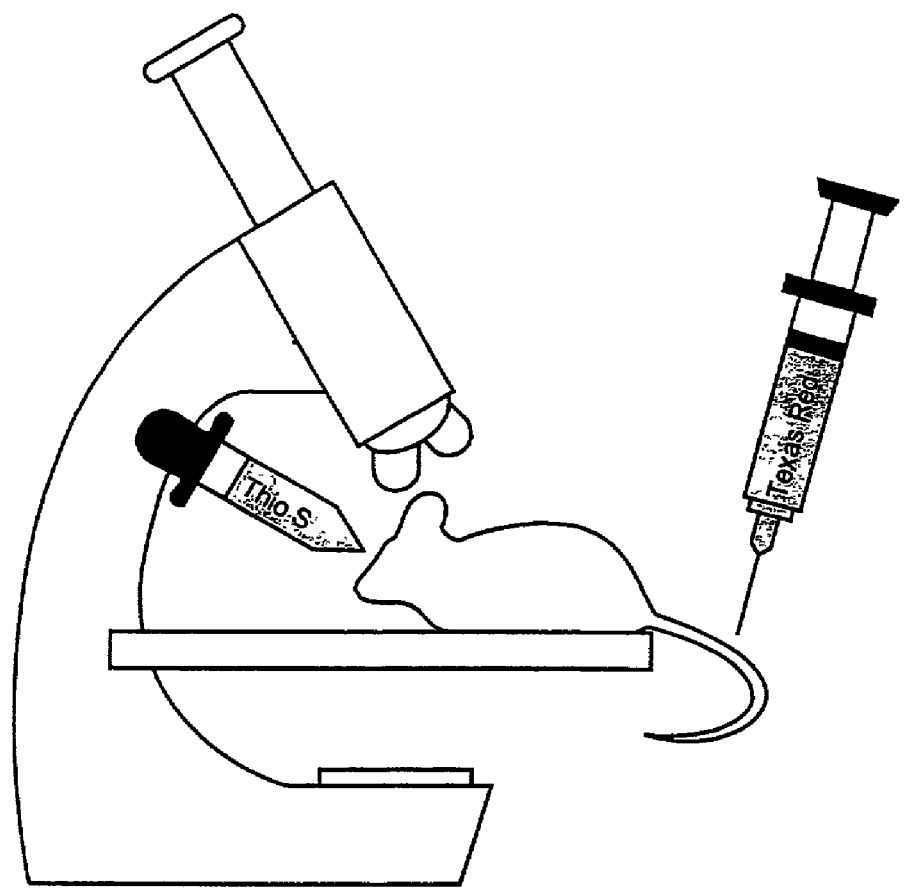
FIG. 8 is a simplified schematic representation of the experimental paradigm. An anesthetized mouse is placed in a head-open device that is then mounted on the stage of a multiphoton microscope. Texas red-labeled dextran is injected in the tail vein as an angiographic contrast agent. Thioflavine-S is applied to the surface of the brain through an open craniotomy. After thioflavine-S is washed out, imaging reveals both microvascular anatomy and amyloid deposits.

With increasing age, the number of thioflavine S positive plaques in the cortex is known to increase (Hsiao, et al., "Correlative Memory Deficits, Aβ Elevation, and Amyloid Plaques in Transgenic Mice," *Science,* 274:99-102 (1996); Irizarry, et al., "APPSw Transgenic Mice Develop Age-Related A Beta Deposits and Neuropil Abnormalities, But No Neuronal Loss in CA1," *J. Neuropathol Exp. Neurol.,* 56:965-973 (1997), which are hereby incorporated by reference in their entirety). Thus, when reimaging a volume of the cortex, one would expect to occasionally find new plaques within the imaging volume. Again, a rigorous criteria was employed to ensure that the appearance of a new plaque did not simply reflect slightly better signal to noise characteristics in a second imaging session than in the first, a greater depth of imaging, or a slightly different imaging volume. Compelling examples nonetheless occurred, in which a new plaque appeared in a volume that had been previously imaged. FIG. 7 shows a dramatic example of a field in which, at the first imaging session there were 3 well defined, characteristic plaques, and at the second imaging session, 64 days later, there were 4.

The in vivo longitudinal data noted above suggest that the average plaque diameter does not vary with age. To examine this conclusion using traditional histological analyses in Tg2576 mice, thioflavine S stained sections from mice were examined either 12 months (n=3) or 22 months (n=3) of age using a Bioquant image analysis system (Hyman, et al., "The Lack of Accumulation of Senile Plaques or Amyloid Burden in Alzheimer's Disease Suggests a Dynamic Balance Between Amyloid Deposition and Resolution," *J. Neuropathol Exp. Neurol.,* 52:594-600 (1993), which is hereby incorporated by reference in its entirety). The average number of plaques in the cortex increases nearly 6-fold over this 10 month period, from 2.3±1.4 to 13.7±4.3 plaques/mm$^2$ (mean±standard deviation, p<0.05). The size distribution of plaque diameters does not change appreciably between 12 months and 22 months, from 18.1±117.8 to 21.4±16.2 micrometers (p>0.05, not significant). These cross-sectional data are consistent with the in vivo measurements, suggesting that plaque size is stable over an extended period of time. Taken together with in vivo measurements, these data are consistent with a model in which plaques are formed and reach their maximal size rather quickly, then stop growing.

In this report, the successful imaging of senile plaques in living transgenic animals using in vivo multiphoton laser scanning microscopy was demonstrated. No other imaging approach has either the resolution, specificity, or sensitivity necessary to observe these Alzheimer's Disease-like lesions. Thus, very little is known about the natural history of these deposits in the living brain. Multiphoton microscopy permits high resolution imaging of living tissue with minimal photodamage or toxicity. Imaging through an intact skull window allows chronic, in vivo brain imaging over periods of days to months. Using thioflavine S, a sensitive and specific fluorescent reporter for senile plaques, a population of identified plaques was followed over time in living transgenic mice. Over periods of days to as long as 5 months, the size and morphology of individual plaques observed by in vivo multiphoton microscopy remain remarkably stable. These results suggest that plaques, once formed, are quickly stabilized. The constancy of the size of plaques over time in the continued presence of soluble Aβ definitively confirms the predictions of the dynamic feedback hypothesis (Hyman, et al., "Quantitative Analysis of Senile Plaques in Alzheimer Disease: Observation of Log-Normal Size Distribution and Molecular Epidemiology of Differences Associated With Apolipoprotein E Genotype and Trisomy 21 (Down Syndrome)," *Proc. Natl. Acad. Sci. USA,* 92:3586-3590 (1995), Cruz, et al., "Aggregation and Disaggregation of Senile Plaques in Alzheimer Disease," *Proc. Natl. Acad. Sci. USA,* 94:7612-7616 (1997), Urbanc, et al., "Dynamic Feedback in an Aggregation-Disaggregation Model," *Phys. Rev. E.,* 60:2120-2126 (1999), and Urbanc, et al., "Dynamics of Plaque Formation in Alzheimer's Disease," *Biophys J.,* 76:1330-1334 (1996), which are hereby incorporated by reference in their entirety). An intriguing avenue of further research is to understand the mechanism and time course of the initial plaque formation. This imaging technique may provide the means for addressing this issue in the future. Likewise, for the first time, shrinkage of individual plaques was observed, confirming the hypothesis that, to some extent, plaques are in a dynamic equilibrium with their environment. This raises the possibility that clearance of plaques, which have heretofore been considered insoluble, may be possible with appropriately targeted therapeutics.

The current observations also raise the new question of why plaques stop growing. It could be speculated that glia promptly respond to the presence of an abnormal deposit in the neuropil either by surrounding it or by phagocytosis. In Alzheimer's Disease, and in the transgenic models studied, glia may play an active role in halting plaque growth primarily by surrounding the deposits (Frautschy, et al., "Microglial Response to Amyloid Plaques in APPsw Transgenic Mice," *Am. J. Pathol.*, 152:307-317 (1998), which is hereby incorporated by reference in its entirety). Recent experiments using immunization with amyloid-β in another transgenic model of Alzheimer's Disease, PDAPP mice, suggest that microglia can phagocytose amyloid deposits if they are decorated with antibodies (Schenk, et al., "Immunization with Amyloid-Beta Attenuates Alzheimer-Disease-Like Pathology in the PDAPP Mouse," *Nature*, 400:173-177 (1999), which is hereby incorporated by reference in its entirety). It is hypothesized that glial interaction with amyloid deposits may be the biological mechanism responsible for the "dynamic feedback" postulated in the theoretical model (Hyman, et al., "Quantitative Analysis of Senile Plaques in Alzheimer Disease: Observation of Log-Normal Size Distribution and Molecular Epidemiology of Differences Associated With Apolipoprotein E Genotype and Trisomy 21 (Down Syndrome)," *Proc. Natl. Acad. Sci. USA*, 92:3586-3590 (1995); Cruz, et al., "Aggregation and Disaggregation of Senile Plaques in Alzheimer Disease," *Proc. Natl. Acad. Sci. USA*, 94:7612-7616 (1997); Urbanc, et al., "Dynamic Feedback in an Aggregation-Disaggregation Model," *Phys. Rev. E.*, 60:2120-2126 (1999); Urbanc, et al., "Dynamics of Plaque Formation in Alzheimer's Disease," *Biophys J.*, 76:1330-1334 (1996), which are hereby incorporated by reference in their entirety), stabilizing the size of plaques and preventing continued growth. Further experiments that specifically inhibit activity of microglia should address this hypothesis directly.

The above data demonstrate the ability to observe amyloid plaques chronically in a living brain using in vivo multiphoton microscopy, which provides resolution on the order of confocal microscopy at unprecedented depths, with negligible tissue damage. This technique will allow longitudinal studies of individual animals subjected to experimental manipulations, and should be particularly powerful for the investigation of therapeutics targeted at clearing amyloid. Likewise, development of fluorophores that identify other pathological features, including non-thioflavine S staining amyloid-β deposits, holds the promise for substantial advances in understanding brain pathophysiology in transgenic models of disease. In principle, this same approach could be utilized to diagnose, and follow, amyloid-β deposition in the human brain in Alzheimer's Disease.

Example 5

Methods

Animals: 10 homozygote PDAPP mice (aged 15-21 months, all female) were used for the in vivo imaging of CAA. These mice overexpress mutant human amyloid precursor protein (APPV717F). The PDAPP transgenic mice were bred from the previously established line PDAPP-109 over several generations on hybrid backgrounds representing combinations of C57BL/6, DBA, and Swiss-Webster strains (previously described in Games et al., 1995).

Preparatory Surgery: Mice were anesthetized with Avertin (Tribromoethanol, 250 mg/kg IP). A small craniotomy (about 1 mm in diameter) was carefully created using a high speed drill (Fine Science Tools, Foster City Calif.) under a dissecting microscope (Leica). The site was moistened with artificial cerebrospinal fluid ("ACSF"; 125 mM NaCl; 26 mM NaHCO$_3$; 1.25 mM NaH$_2$PO$_4$; 2.5 mM KCl; 1 mM MgCl$_2$; 1 mM CaCl$_2$; 25 mM glucose) and the dura gently peeled away from the surface of the brain.

Imaging Agents: Thioflavine S (0.005% ThioS in ACSF, Sigma Chemical, St Louis Mo.) was topically applied to the site in order to label ThioS positive amyloid deposits. Texas red labeled 70,000 MW dextran, which does not cross the blood-brain barrier (Molecular Probes, Eugene, Colo.), was intravenously injected into the tail vein of the mice in order to visualize the lumen of blood vessels and obtain a fluorescent angiogram. Both agents were applied 20 minutes prior to imaging.

In vivo Imaging: Imaging was carried out as described above, except that an incremental z-step of 5 µm was used to generate a 3 dimensional stack of images from the skull surface to a depth of about 200 µm into the brain.

Image Processing: Images were examined as a single stack of images using Scion Image (Scion Corp, Frederick Md.) and ImageTool (University of Texas Health Science Center, San Antonio, Tex.). Images were reconstructed in 3 dimensions in order to examine vascular structures via Texas Red angiograms, and vessel associated, ThioS amyloid deposits, then collapsed into an XY projection. Portions of angiograms that were technically inadequate (e.g. at the deepest optical planes) were excluded prior to analysis.

Quantitative Analysis of Images: In order to determine the effect of Aβ on vessel diameter, the widths of all vessels were analyzed with clear angiograms and a detectable amount of amyloid angiopathy. The diameters of the internal lumen of these vessels were measured every 30 µm along their length starting at a random point (i.e., systematic random sampling (Gundersen et al., "The New Stereological Tools: Disector, Fractionator, Nucleator and Point Sampled Intercepts and Their Use in Pathological Research and Diagnosis," *Apmis* 96:857-81 (1988), which is hereby incorporated by reference in its entirety). At each point of measurement, the vessel segment was noted as either being affected or unaffected by Aβ, and used a semiquantitative scale (0=none, +=mild; ++=moderate, +++=severe) to assess the extent of Aβ deposition (FIG. 9).

To test the hypothesis that Aβ deposits tend to occur near branch points of vessels, a selection of points in space, 100 µm apart, were systematically sampled and overlayed on the images. For every point that overlapped a vessel, it was noted whether that part of the vessel was affected or unaffected by Aβ. The distance from this point to the nearest branch point on that vessel was also mesured.

Example 6

Concurrent Imaging of Aβ and Microangiography

Thio S, which is a green fluorophor, and Texas red, a red fluorophor, can be detected simultaneously with available filter sets. Both fluoresce brightly with exposure to 750 nm excitation with a mode-locked Ti sapphire laser. A 3 dimensional stack of optical images, approximately 615×615×200 µm deep, was collapsed for further analysis. FIG. 9 shows the vessel lumen, and the circumferential deposits of Aβ that stain with thio S. Because these are collapsed images, occasionally they overlap in the images; in individual cross sections, the thio S staining always surrounds the Texas red column and does not overlap.

Figure 10:
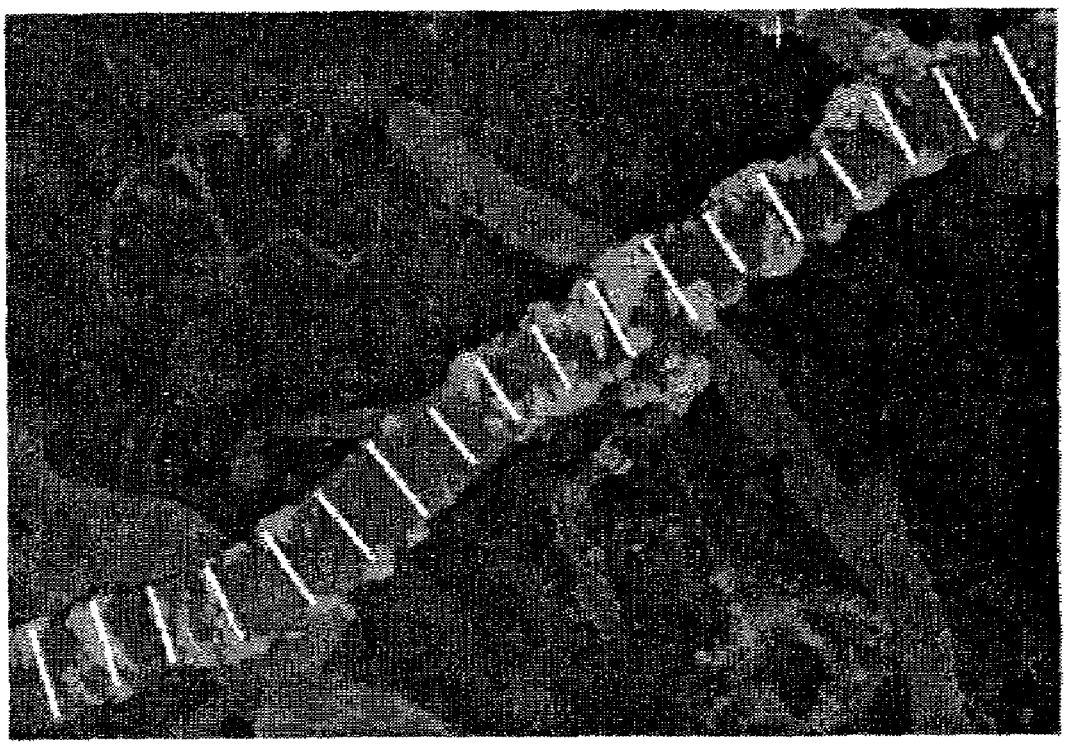
FIG. 10 shows the measurement of vessel diameter. A random start point was placed, and then the diameter of vessels measured every thirty micrometers thereafter throughout the image series. At each measuring point, the diameter of the vessel as well as the presence or absence of amyloid was noted.
Figure 11:
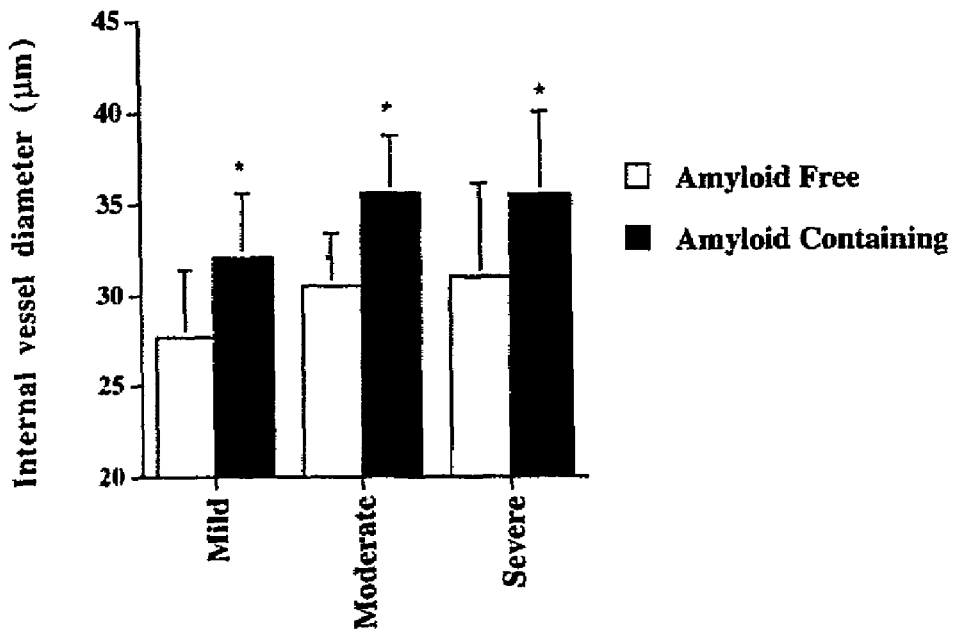
FIG. 11 shows the measurement of vessel diameter as noted with regard to FIG. 10. There is a significant difference between amyloid-containing and non-amyloid-containing vessels for mild (n=11), moderate (n=10) and severe (n=6) vessels.

To examine the effect of Aβ on vessel physiology, vessel diameter was measured. It is clear that some vessels contain Aβ in part of the vessel, but not in other parts. This discontinuity of Aβ deposition is a hallmark of amyloid angiopathy clinically, and is replicated in the transgenic model. Using a random start position, diameter was measured every 30 µm along the vessel (FIG. 10). This represents an adaptation of the stereologically-based "systematic random sampling" approach. A semiquantitative score was assigned for each point. The vessel segments containing Aβ amyloid were compared to vessel segments not containing amyloid in each vessel. Thus, the vessel serves as its own "control". Using this analysis, it was found that the portions of the vessel segments that contained thio S positive staining were approximately 16% larger than vessel segments without Aβ (p<0.001, paired t test). Surprisingly, there was no clear indication that severity of vessel changes worsened this effect (FIG. 11). For example, in those vessels where the amyloid angiopathy was just "mild", the control vessel segment had an average internal diameter of 27.7 μm, whereas the amyloid-containing vessel had an internal diameter of 32.1 μm (p<0.01). Of interest, the severely affected blood vessels had only slightly larger diameters, 30.8 μm for non-amyloid-containing and 35.5 μm for amyloid-containing segments (p<0.005).

This in vivo imaging also provided a unique three-dimensional data set in which to examine the relationship of amyloid deposits around blood vessels with the architecture of the vasculature. In initial imaging sessions, the frequency with which amyloid deposits appeared to occur at or near branch points of vessels was striking (FIG. 12). To test this idea, a random sampling method was developed to evaluate the likelihood that amyloid deposits were, in fact, more likely to be close to branch points than not. A sample grid was overlaid with a probe located every 100 μm over the images. If a probe happened to overlap a blood vessel, that vessel segment was rated as having (or not having) amyloid deposits, and the distance from that point on the vessel to the closest branch points was measured. Only vessels that contain some Aβ were included in this analysis, because it was not possible to ascertain with certainty whether vessels that did not contain amyloid were small arterioles or venules. It was assumed that vessels with "mild" changes were most likely in the "early" phase of amyloid deposition, and that vessels with moderate-to-severe changes are in later stages. If so, it was predicted that amyloid-containing segments in mild vessels would appear to be "closer" to branch points than those in moderate or severe cases if the amyloid deposition tended to start near a branch point and then "fill in" more and more of the vessel. The data support this hypothesis. Among vessels affected by mild amounts of Aβ, vessel segments that contained amyloid were significantly closer to vessel branches than unaffected vessel segments (62±10 μm (mean±SE) for Aβ-containing vessel segments versus 133±17 μm for non-Aβ-containing segments, p<0.005, t-test) (FIG. 13). Among vessel segments affected by moderate degrees of Aβ deposition, vessel segments containing Aβ were also closer to vessel branches than unaffected vessel segments, but the absolute distance to the branch point is increased compared to mildly affected vessels. The median distance was 84±10 μm for Aβ-containing vessels versus 148±21 μm for non-Aβ-containing vessels (p<0.005). Interestingly, among the severely affected vessels where almost the entire length of the vessel wall was affected by amyloid angiopathy, the relationship between the presence of amyloid and relative closeness to a branch point was less evident (116±15 μm vs 160±26 μm, not significant).

In this study, a novel optical imaging technique, in vivo multiphoton microscopy, was used to examine the consequences of amyloid deposition on blood vessels in living transgenic mice. Several new observations were described as follows: even mild degrees of cerebral amyloid angiopathy lead to an alteration in vessel anatomy in vivo, with a statistically significant dilation of the vessel; this appears to be the case in a graded fashion, with increasing amounts of amyloid there is increased vessel dilation. This result shows directly an impairment in vessel physiology in vessels affected by congophilic amyloid angiopathy ("CAA"). Because this effect is seen in mildly affected vessels, it is not due to the direct smooth muscle cell loss seen in advanced CAA in humans (Vonsattel et al., "Cerebral Amyloid Angiopathy Without and With Cerebral Hemorrhages: A Comparative Histological Study," *Ann Neurol* 30:637-49 (1991) and Kawai et al., "Degeneration of Vascular Muscle Cells in Cerebral Amyloid Angiopathy of Alzheimer Disease," *Brain Res* 623:142-6 (1993), which are hereby incorporated by reference in their entirety). Preliminary studies using phalloidin staining as a marker for smooth muscle cells shows that the density of smooth muscle cell in vessels containing mild amyloid angiopathy does not differ from vessels that are normal.

Moreover, preliminary studies in Tg2576 transgenic mice that also develop amyloid angiopathy suggests an impairment of pharmacologically induced dilation in vessels that contain CAA. Another mouse line that overexpresses human APP (Swedish mutation), on an FVB background, did not develop Aβ deposits but did show impairments of endothelial-dependent changes in cerebral blood flow (Iadecola et al., "SOD1 Rescues Cerebral Endothelial Dysfunction in Mice Overexpressing Amyloid Precursor Protein," *Nat Neurosci* 2:157-61 (1999), which is hereby incorporated by reference in its entirety). Aβ peptide has also been described to have both toxic effects on endothelial cells, and smooth muscle cells (Eisenhauer et al., "Toxicity of Various Amyloid Beta Peptide Species in Cultured Human Blood-brain Barrier Endothelial Cells: Increased Toxicity of Dutch-type Mutant," *J Neurosci Res* 60:804-10 (2000) and Van Nostrand et al., "Cerebrovascular Smooth Muscle Cell Surface Fibrillar A Beta. Alteration of the Proteolytic Environment in the Cerebral Vessel Wall," *Ann N Y Acad Sci* 903:89-96 (2000), which are hereby incorporated by reference in their entirety) as well as vasoactive properties (Thomas et al., "Beta-Amyloid-mediated Vasoactivity and Vascular Endothelial Damage," *Nature* 380:168-71 (1996), Wirth et al., "Amyloid Beta-(1-40) Stimulates Cyclic GMP Production Via Release of Kinins in Primary Cultured Endothelial Cells," *Eur J Pharmacol* 382:27-33 (1999), and Suo et al., "A Beta Vasoactivity In Vivo," *Ann N Y Acad Sci* 903:156-63 (2000), which are hereby incorporated by reference in their entirety). Taken together with the results described here, these data strongly suggest that the deposition of Aβ in microvessels causes an alteration in the integrity of microvascular responsiveness in vivo.

Multiphoton microscopy also provided the opportunity to evaluate a fairly large 3-dimensional reconstruction of the cerebral vasculature at unprecedented levels of resolution. In the XY plane, the resolution of multiphoton microscope, as it was configured, is approximately 1 μm. Thus, in vivo fine capillary structures deep to the surface of the brain was detected. Quantitative evaluation of the reconstructions suggested that, in cases of mild amyloid angiopathy, the amyloid tended to occur near branch points of vessels. This is an intriguing observation, which would have been difficult to detect in histological cross-sections, and is reminiscent in some ways of the atherosclerotic process. This association suggests that unique vascular factors are likely important in initiating amyloid deposition, potentially including issues such as microturbulence within the vessel, or subtle changes in vessel morphology near branching structures. The extent to which amyloid is selectively near branch points diminishes with increasing severity of CAA, until this effect disappears in severe CAA. It is anticipated that, using multiphoton microscopy over extended periods of observation (months), the progression of amyloid deposits over time can be followed and the possibility that vascular remodeling occurs can be evaluated.

Example 7

Transgenic Mice

Tg2576 mice expressing hAPP(Sw) under the hamster prion protein promoter were obtained from a colony started with a breeding pair. These animals have been shown to develop age-dependent amyloid angiopathy as well as cortical and hippocampal amyloid plaques similar to those seen in AD (4). Eight animals carrying the transgene and eight non-transgenic littermates were used for the anatomical measurement of smooth muscle cells ("SMCs") in pial vessels. Mice of each genotype were of two age groups, a young group at 6 months of age, and an older group at 14 months of age (Table 1).

The thioS and Alexa-568 signals fell clearly into the first two and third channels, respectively.

Example 9

Smooth Muscle Cell Density Measurement

Series of 60× optical sections spaced 2 µm apart were taken through branches of the anterior and middle cerebral arteries on the dorsal aspect of the intact brain. Each optical section was acquired at slow scan speed, with Kalman filtering of two successive scans for noise reduction. Vessel structure was then reconstructed by a maximum intensity projection of the stack of optical sections. A computer-generated index line of random length was drawn perpendicular to the vessel diameter (Scion Image). Linear SMC density was calculated as the number of SMCs along this line divided by the length of the line in microns. Three vessels were measured from each animal; in order to minimize distortion of the measured SMC

TABLE 1

| Group | Age (months) | n | pH | Blood $CO_2$ (mmHg) | Blood $pO_2$ (mmHg) | Mean PB pre (mmHg) | Mean BP Post (mmHg) | Vessel diameter (µm) |
|---|---|---|---|---|---|---|---|---|
| 6 month Tg− | 5.3 ± 0.6 | 3 | 7.41 ± 0.01 | 30.6 ± 3.4 | 169.2 ± 57.8 | 95.0 ± 5.6 | 91.7 ± 4.7 | 25.7 ± 2.3 |
| 6 month Tg+ | 6.3 ± 0.6 | 3 | 7.32 ± 0.05 | 37.5 ± 6.0 | 127.6 ± 20.7 | 72.0 ± 13.0 | 64.7 ± 18.0 | 28.3 ± 0.6 |
| 14 month Tg− | 13.7 ± 1.2 | 3 | 7.39 ± 0.06 | 33.0 ± 4.5 | 166.6 ± 23.0 | 66.0 ± 11.0 | 62.7 ± 12.7 | 31.3 ± 6.4 |
| 14 month Tg+ | 14.0 ± 2.6 | 5 | 7.33 ± 0.09 | 33.4 ± 3.2 | 149.0 ± 22.7 | 65.0 ± 7.6 | 61.3 ± 3.2 | 28.3 ± 2.9 |

These same groups of animals were used for the vessel reactivity experiment. Additionally, amyloid deposition and SMCs were imaged in an older group of three transgene positive animals, aged 24.7±2.3 months.

Example 8

Smooth Muscle Cell Imaging

Following in vivo vascular reactivity measurements, animals were sacrificed by an overdose of anesthetic (halothane). Intact crania were removed and fixed in paraformaldehyde (4% in TBS) for several days. The presence of the intact skull and craniotomy identified the same population of vessels whose dilation was measured in vivo. The brain was then removed, washed with TBS, treated with 0.5% Triton-X in TBS for 20 min, washed again, then incubated in 1% bovine serum albumin (BSA) in TBS for 20 minutes to minimize non-specific background staining. Vessels were stained with a combination of Alexa-568 phalloidin (Molecular Probes, Eugene, Oreg.) (50 ul stock solution/2 ml) and thioflavine S (thio S, Sigma, St. Louis, Mo.) (0.005%) in 1% BSA in TBS. After 20 min in the staining solution, the brains were washed with TBS, and stabilized within a plastic dish with molten bone wax. The brains were covered in TBS, into which a dipping microscope objective was lowered for imaging.

A BioRad 1024MP multiphoton imaging system with a Ti:Sapphire laser (Spectra Physics) operating at 750 nm, with an output power of 25 mW at the back aperture of the objective, was used for imaging. The system was mounted on an upright Olympus BX-50 microscope, equipped with long working distance dipping objectives (10×, NA 0.5; 60×, NA 0.8). External detectors were used to enhance detection of emitted light. The filter set used separated emitted light into three channels: 360-430 nm, 485-505 nm, and 525-650 nm.

density by a sloping vessel, the selected vessels were those whose longitudinal axis most nearly matched the imaging plane. While the obvious presence of amyloid on the vessels made blind selection with respect to genotype impossible, the measurement of phalloidin-stained SMCs was blind with respect to the age of the animal imaged.

Example 10

Animal Preparation for Vascular Reactivity Measurement

All experiments were conducted in accordance with National Institutes of Health and Massachusetts General Hospital Institutional guidelines. Animals were allowed food and water ad libitum. Anesthesia was induced with 2.5% halothane and maintained in 1.0% halothane in 67% $N_2O$ and 33% $O_2$. Mice were intubated transorally, placed in a stereotaxic frame and ventilated artificially (SAR-830/P, CWE, Ardmore, Pa.). End-tidal $CO_2$ was continuously monitored by a microcapnometer (Columbus Instruments, Columbus, Ohio). The femoral artery and vein were cannulated with a polyethylene catheter (PE-10, Intramedic, Becton Dickinson) for continuous arterial blood pressure and heart rate monitoring and for drug infusion. Alpha-chloralose (80 mg/kg i.v.) was injected and halothane was withdrawn gradually for deepening of anesthesia. Supplemental doses of alpha-chloralose were given as needed to maintain a stable level of anesthesia, which was periodically tested by arterial blood pressure and heart rate response to tail pinch. Arterial blood gas and pH were analyzed before drug superfusion. Rectal temperature was maintained at 37° C. with a thermostatically controlled mat (temperature control, FHC, Brunswick, Me.).

Example 11

Closed Cranial Window Preparation

Techniques used for measurement of vessel diameter changes in mice were similar to those described. The head was fixed in a stereotaxic frame, and the skull exposed by a longitudinal skin incision. A stainless steel cranial window ring (7.0 mm inner diameter, 1.7 mm in height) containing three flow ports was adhered to the skull in a loop of bone wax. A craniotomy (2×1.5 mm) was made in the left parietal bone within the ring of the window. The dura was then opened while the brain surface was superfused with artificial cerebrospinal fluid ("ACSF"). A cover glass was placed on the ring and affixed with dental acrylic. The ports were attached to inflow and outflow connections, allowing for superfusion of solutions directly onto the exposed brain; the volume under the window was approximately 0.1 ml. ACSF was as follows (in mMol/L): $Na^+$ 156.5, $K^+$ 2.95, $Ca^{++}$ 1.25, $Mg^{++}$ 0.67, $Cl^-$ 138.7, $HCO_3^-$ 24.6, dextrose 3.7 and urea 0.67. ACSF was kept at pH 7.35-7.45 by equilibration with 6.5% $CO_2$, 10% $O_2$, and 83.5% $N_2$. ACSF was circulated by an infusion pump (0.4 ml/min) via PE-50 tubing connected to the inlet port. Intracranial pressure was maintained at 5-8 mm Hg by adjusting the outlet tubing to an appropriate height above the level of the window; ACSF temperature within the window was maintained at 36.5-37.0° C.

Example 12

Vessel Diameter Measurement

Pial vessels were visualized with a video microscope system comprised of an intravital microscope (Leitz, Germany), CCD video camera (model 1300, Cohu Inc, San Diego, U.S.A.), a camera controller (C2400, Hamamatsu Photonics, Hamamatsu, Japan), video monitor (Sony, Japan), and a video recorder (Panasonic, Japan). The images were continuously recorded on videotape. The diameter of a single pial arteriole (20-30 µm) was measured per experiment by a video width analyzer (C3161, Hamamatsu Photonics) and recorded using the MacLab data acquisition and analysis system. ACSF was superfused for 20-30 min until a stable baseline diameter was obtained. Acetylcholine ("ACh") (10 and 25 µM) and sodium nitroprusside (SNP, Sigma) (0.5 µM) dissolved in ACSF were then applied to assess vessel dilation. Drugs were superfused for 10 min, followed by ACSF superfusion for an additional 20 min for washout and return to baseline vessel diameter. The order of application of the two drugs was chosen at random. In a subset of animals (n=6), two cumulative concentrations of ACh were superfused, without return to baseline between the low and high doses. For each application of drug, the maximum diameter change from baseline was compared. Vessel imaging and data analysis were performed without experimenter knowledge of the genotype or age of animal. Animals that exhibited significant hypotension (n=2) or hypercapnia (n=1) during the procedure were eliminated a priori from analysis.

To assess the effect of this amyloid deposition on the structure of the vessel wall, SMCs were visualized in conjunction with amyloid using a combination of fluorescently tagged phalloidin and thioflavin S (thioS). Phalloidin binds to actin filaments, particularly F-actin, and has been used to visualize SMCs under a variety of conditions (Wilson et al., "A Pulmonary Artery Endothelial Factor Causes Unidirectional Alignment of Smooth Muscle Cells," *Tissue Cell* 19:177-828 (1987) and Kobayashi et al., "Emergence and Distribution of Intimal Smooth Muscle Cells in the Postnatal Rat Aorta," *Cell Tissue Res* 289:487-97 (1997), which are hereby incorporated by reference in their entirety). Phalloidin stains vascular SMCs in fixed mouse pial vessels, and, conjugated to Alexa 568, can be imaged in a separate emission channel from thioS. In this way, the organization and number of SMCs in a length of pial arteriole can be studied relative to the surrounding amyloid. Staining could be accomplished in intact, fixed brains and three-dimensional imaging carried out with MPSLM.

FIG. 14 shows the pattern of amyloid angiopathy on leptomeningeal vessels of a 16 month old Tg2576 mouse. This montage of 32 images illustrates how the involvement of the middle cerebral artery varies along its length, and is typical of all vessels examined. The larger caliber portion of the vessel appears to be the earliest and most severely affected, with the amyloid forming complete rings around the circumference of the vessel. The classic segmental appearance of the amyloid is evident, and in the most severely affected portions of the vessel, the amyloid continues uninterrupted for stretches of several hundred microns. Smaller size vessels have less amyloid, with sparser deposits, sometimes amounting to isolated slivers of amyloid on the vessel wall. Amyloid deposition appeared exclusively on the walls of arterioles, while venules, whose silhouettes appear in the figure background, remained unaffected.

Figure 15:
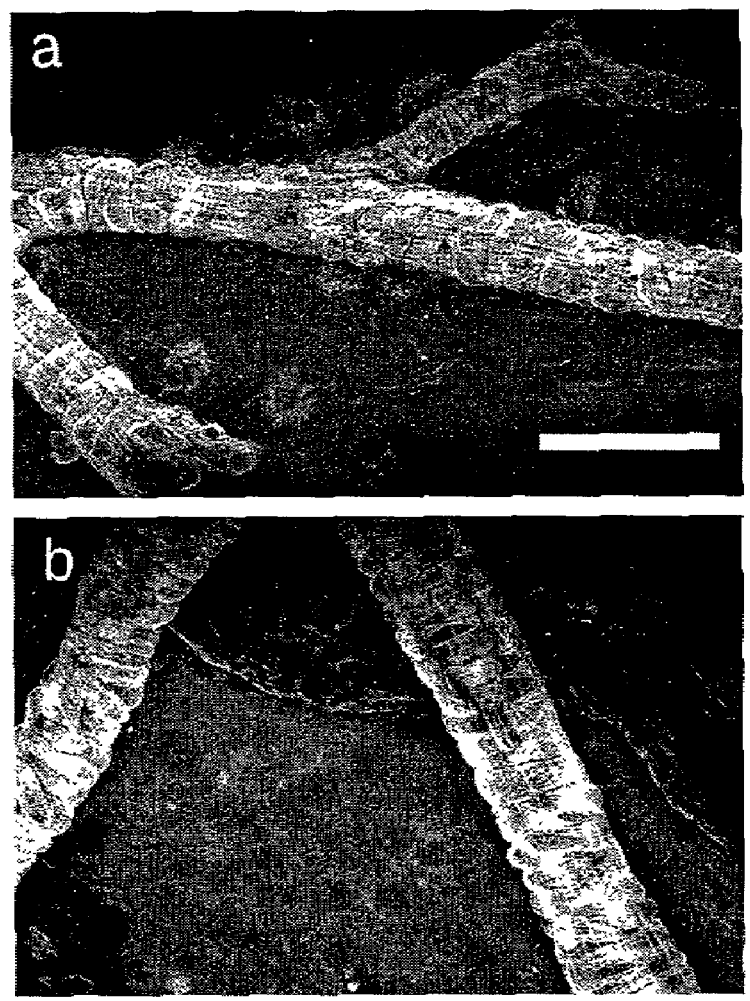

The morphology of SMCs in amyloid angiopathy was studied at three ages. Non-transgenic littermates and transgenics too young for amyloid deposition (6 months) showed orderly arrangement of SMCs. SMCs were arranged circumferentially around the vessel, and packed adjacent to one another along the length of the vessel with no apparent space between them (FIG. 15).

Figure 16:
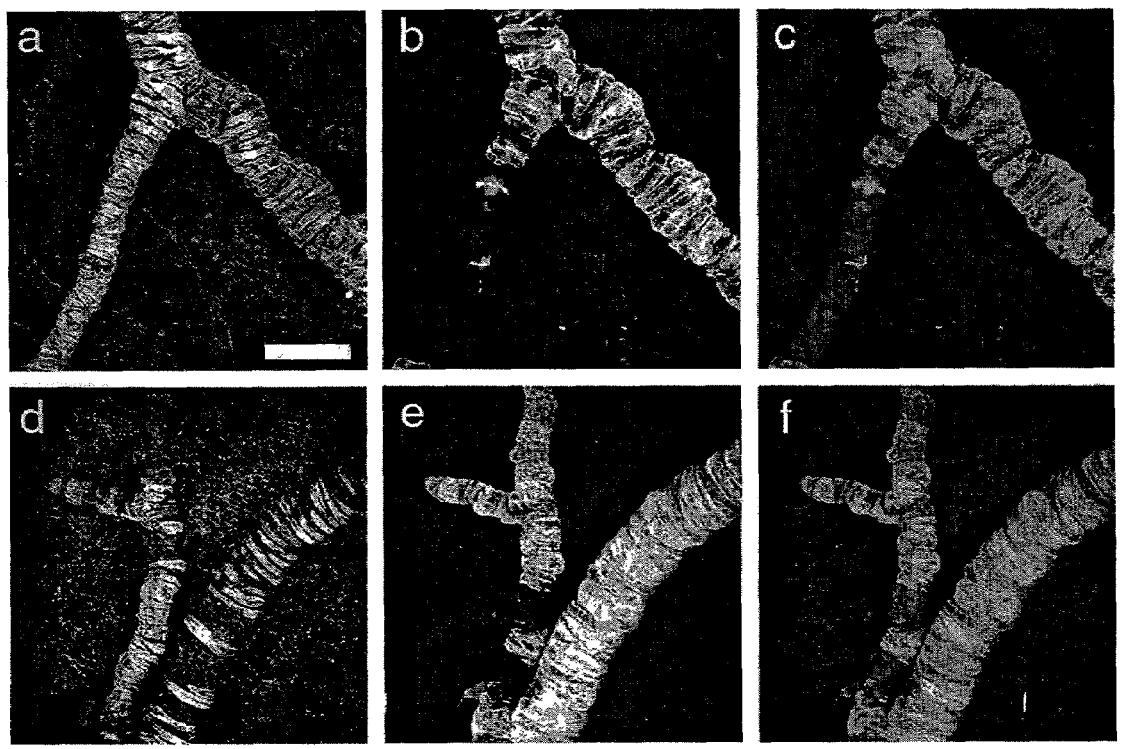

By contrast, thioS-positive amyloid substantially disrupts SMCs in 14-month and 24-month transgenic animals (FIG. 16). Regions of sparse amyloid were characterized by shards of thioS-positive material between neighboring SMCs. More heavily affected portions of vessels showed amyloid encasing individual SMCs, distancing and eventually completely isolating them from neighboring cells. While the organization of SMCs in affected vessels of the 14-month-old group was clearly abnormal (FIGS. 16A-B), SMCs seemed to have accommodated encroaching amyloid by contracting along their lateral dimension; SMC loss was not apparent along the length of the vessel. In accord with these qualitative observations, quantitative analysis (FIG. 17) showed that there was no significant change in the linear density of SMCs within thioS-positive portions of vessels compared to thioS-negative portions of vessels in 14 month Tg2576 animals or compared to measurements in non-transgenic littermate controls.

The oldest group of animals studied (24 months), however, did lose SMCs along the length of the vessel in the areas of heaviest amyloid deposition (FIGS. 16C-D). The density of SMCs along the length of the vessel was calculated for portions of vessels affected and unaffected by amyloid; by 24 months of age, amyloid-laden vessels lost over half the SMCs relative to unaffected vessels from the same animals. The SMC density in amyloid-free vessels or portions of vessels was not significantly different between the 14 month old and 24 month old age groups (FIG. 17), nor did it differ significantly from SMC density in vessels from non-transgenic 14 month old, non-transgenic 6 month old, or transgenic 6-month old animals. Subsequent examination of Nissl stained histological sections revealed preservation of endothelial cells even in severely affected portions of the vessels. No evidence for hemorrhagic strokes was observed.

Loss of SMCs in the vessel wall, as seen in the 24-month-old animals, is certain to alter dilation in response to physiologic or pharmacological stimulation; the consequence of disruption of SMCs, as seen in the 14-month-old animals, is unknown. It was hypothesized that the presence of amyloid in the vessel wall would impair vessel function even before SMC loss. Therefore, the physiology of pial vessels was directly examined, using a closed cranial window preparation in the young (6 months) and older (14 months) transgenic and nontransgenic littermate control animals. The change in vessel diameter to application of either acetylcholine ("ACh"), which causes endothelial-dependent vasodilatation through a nitric oxide-dependent mechanism (10), or sodium nitroprusside ("SNP"), a nitric oxide donor that acts directly on SMCs (FIG. 17), was measued. To test the possibility that overexpression of the APP gene and overproduction of Aβ peptide has an effect on vessel function independent of amyloid deposition, vessel response in the 6-month-old transgenic and non-transgenic animals were also measured. The physiological parameters of the four measured groups are shown in Table 1. No significant differences were observed for arterial blood pH, $CO_2$, $O_2$, or baseline vessel diameter for the four groups (p>0.05, ANOVA). A significant difference was seen between the arterial blood pressure measurements for the young non-transgenic group and those for the other three groups (p<0.05, ANOVA), with the blood pressure both before and after vessel reactivity measurement being substantially higher in this younger group. No difference was seen, however, between the mean blood pressure before the experiment and the blood pressure after the experiment for any of the experimental groups.

The percentage dilation to application of ACh and SNP for the four groups is shown in FIG. 18. No difference in the response to either ACh or SNP was observed between the 6-month-old Tg+ and Tg– groups. By contrast, in the 14-month-old animals, vessel dilation was markedly attenuated in response to both doses of ACh and to SNP in four out of five transgenic animals as compared to the non-transgenic group. Vessel dilation in these animals, in fact, was reduced to about 25% that of control animals. One outlier in the transgene positive group showed essentially normal responses to both ACh and SNP, values that were six SDs away from the mean of the remaining members of the transgene-positive group. No difference in any of the physiological parameters of this individual animal could account for this remarkable discrepancy from other group members.

After physiologic study, the animals were perfused and prepared as noted above for detailed MPLSM analysis. On imaging, the vessels in the 14 month old "outlier" were moderately involved with thioS-positive amyloid in the measured vessel segment, not dissimilar from other members of the group, though lacking the complete rings of amyloid present in the most severely affected vessels. Exclusion of data from this outlying animal results in highly significant (p<0.005, ANOVA) difference between the transgenic animals and non-transgenic littermates for both doses of ACh and for SNP. Inclusion of this outlier results in a more modest, but significant result for the $10^{-5}$M administration of ACh (p<0.05), and non-significant differences for the higher dose of ACh and for SNP.

Using Tg2576 transgenic mice, the natural history of Aβ deposition in cerebral vessels was examined and the hypothesis that amyloid deposition leads to both structural and functional disruption of affected vessels was tested.

The data indicate that amyloid-associated disruption of SMCs impairs response to both endothelial-dependent and endothelial-independent vasodilators at an age predating loss of SMCs in these vessels. Several possibilities for the mechanism of this interference of amyloid with vessel function exist. Amyloid may present a mechanical obstacle to vessel dilation, rendering the vessel wall relatively rigid. This possibility is supported by the long-standing observation that vessels with amyloid angiopathy fail to collapse in postmortem tissue, giving them the classic "stove-pipe" appearance (Vonsattel et al., "Cerebral Amyloid Angiopathy Without and With Cerebral Hemorrhages: A Comparative Histological Study," *Ann Neurol* 30:637-49 (1991), which is hereby incorporated by reference in its entirety). The same inflexibility that maintains vessel diameter postmortem may physically restrict dilation in vivo. Alternatively, physical separation of adjacent SMCs by amyloid may disrupt contraction dependent on their coordinated action. A third possibility, given that the accumulation of amyloid around these vessels ultimately results in significant death of SMC, may be a low-grade toxicity of amyloid on the SMC that interferes with their ability to dilate appropriately, perhaps by altering expression of channel proteins (e.g., $Ca^{++}$-dependent $K^+$ channels (Taguchi et al., "ATP-sensitive K+ Channels Mediate Dilatation of Cerebral Arterioles During Hypoxia," *Circ Res* 4:1005-8 (1994), which is hereby incorporated by reference in its entirety) mediating NO-dependent relaxation in cerebral vessels (Sobey et al., "Effect of Nitric Oxide and Potassium Channel Agonists and Inhibitors on Basilar Artery Diameter," *Am J Physiol* 72:H256-H262 (1997), which is hereby incorporated by reference in its entirety). Amyloid is toxic to endothelial cells in culture (Thomas et al., "Beta Amyloid-mediated Vasoactivity and Vascular Endothelial Damage," *Nature* 80:68-71 (1996), which is hereby incorporated by reference in its entirety), and a mutant form of the Aβ peptide is toxic to SMCs in culture, although the 1-40 form that predominates in the Tg2576 mouse did not demonstrate direct toxicity to SMCs (Davis et al., "Enhanced Pathologic Properties of Dutch-type Mutant Amyloid Beta-Protein," *Proc Natl Acad Sci USA* 3:2996-3000 (1996) and Wang et al., "Toxicity of Dutch (E22Q) and Flemish (A21G) Mutant Amyloid Beta Proteins to Human Cerebral Microvessel and Aortic Smooth Muscle Cells," *Stroke* 31:534-538 (2000), which are hereby incorporated by reference in their entirety). The clear in vivo loss of SMC function, then, may reflect a preliminary stage in a cascade of events that lead to cell loss. The SMC loss seen in the Tg2576 mouse model of amyloid deposition parallels that previously described at the ultrastructural level in postmortem human AD cases (Vinters et al., "Microvasculature in Brain Biopsy Specimens from Patients with Alzheimer's Disease: An Immunohistochemical and Ultrastructural Study," *Ultrastruct Pathol* 18: 333-48 (1994), which is hereby incorporated by reference in its entirety). Intriguingly, such a model of amyloid-induced SMC dysfunction presents the possibility of restoring vessel function, if the amyloid can be cleared before SMC loss in affected vessels. The development of therapeutic approaches for amyloid clearance (Schenk et al., "Immunization With Amyloid-beta Attenuates Alzheimer-disease-like Pathology in the PDAPP Mouse," *Nature* 00:173-7 (1999), which is hereby incorporated by reference in its entirety) should enable the testing of this hypothesis in these animals.

Cerebral vessel function has been previously studied in mice overexpressing APP(Sw) on an FVB background (Tg1130H). These mice do not develop amyloid deposits, and die at a relatively young age. In contrast to the present results, the Tg1130H mice showed impaired endothelial-dependent, but not endothelial-independent, changes in cerebral blood flow (Iadecola et al., "SOD1 Rescues Cerebral Endothelial Dysfunction in Mice Overexpressing Amyloid Precursor Protein," *Nat Neurosci* 2:57-61 (1999), which is hereby incorporated by reference in its entirety). Differences in the age, background strain (the Tg2576 are on a C57 B/J1 F1 background), or the exact measurement protocols (blood flow versus vessel diameter) might also contribute to observed differences. Taken together, however, the data demonstrate profound impairment of the functional integrity of cerebrovascular responses due to over-expression of mutant APP and Aβ deposition, and imply that functional alterations are also likely to occur in CAA and Alzheimer's Disease. These in vivo results, together with observations that Aβ has a positive ionotropic effect on aortic rings studied ex vivo (Paris et al., "Soluble Beta-amyloid Peptides Mediate Vasoactivity Via Activation of a Pro-inflammatory Pathway," *Neurobiol Aging* 21:183-97 (2000) and Crawford et al., "Characteristics of the In Vitro Vasoactivity of Beta-amyloid Peptides," *Exp Neurol* 150:159-68 (1998), which are hereby incorporated by reference in their entirety), support the hypothesis that vessel-associated Aβ causes a physiologically relevant impairment of cerebrovascular vessel structure and function.

Example 13

Methods

These experiments follow on the observation that immunization of PDAPP mice with amyloid-β leads to the development of antibodies against amyloid-β, and to the subsequent prevention of new amyloid-β deposits (Schenk et al. *Nature* 400:173-7 (1999), which is hereby incorporated by reference in its entirety). The hypothesis that interaction of an anti-amyloid-β antibody with a plaque in vivo would lead to its clearance was tested. It was, therefore, attempted to image amyloid-β deposits in vivo prior to, and after therapeutic intervention. A fluorescently labeled anti-amyloid-β antibody was applied directly to the cortex. Initial imaging of the cortex in a living 20 mo. old PDAPP mouse homozygote for the mutant APP transgene revealed numerous amyloid-β deposits, some of which had the characteristics of diffuse amyloid, some of which had discrete cores. A stack of optical thin sections, in 2 micron steps, was obtained up to ~100-150 microns deep to the brain surface (FIGS. 19A and C). Three dimensional reconstruction of the images (Voxblast, VayTek, Fairfield Iowa) on a Windows-NT based workstation (Precision 610, Dell Computer, Round Rock Tex.) revealed extraordinary details of the amyloid-β deposits, even more than 100 microns deep to the brain surface. The diffuse deposits had a fine morphology with frequent extensions, irregular shapes, and clusters identical to the image observed by conventional histological immunostaining of PDAPP mice. Amyloid angiopathy was similarly imaged surrounding some pial vessels. Thus, fluorescently labeled anti-amyloid-β antibodies applied to the surface of the cortex diffused into the cortex and specifically labeled amyloid-β deposits. This labeling allowed existing deposits to be identified and imaged by multiphoton microscopy.

The animal recovered without incident after imaging. Three days later the animal was reanesthetized and the same volume was imaged. Texas red angiography and stage location assured that the exact same volume was being imaged. Initial imaging showed that very little or no detectable fluorescence remained from the imaging session three days previously. Fluorescently labeled anti-amyloid-β antibody was then re-applied directly to the cortex. Repeat imaging of a Z series of images, obtained every 2 microns from the surface of the cortex to 100 to 150 microns deep, was obtained. Imaging showed few or none of the amyloid-β deposits that were present at the initial imaging, but amyloid angiopathy was still detected (FIGS. 19B and D). Thus, at this time point after a single application of anti-amyloid-β antibody, a dramatic resolution of amyloid-β deposits was observed. Replication of this experiment with delays after initial imaging of 3 to 8 days, in one or two sites in each of six of six animals showed nearly identical results. To examine the possibility that 10D5 was simply masking the amyloid-β during the second imaging session, imaging during the second imaging session with 3D6, an antibody directed against a distinct epitope on the N terminus of amyloid-β, was performed with identical results. These results suggest that the amyloid-β present in the first imaging session was reversed, i.e. that it was cleared by application of the antibody.

An alternative explanation was explored: that removal of the skull and dura, application of a monoclonal antibody, and imaging could have had a nonspecific effect on the amyloid-β deposits. To address this possibility, sham experiments were carried out in five animals in which the initial imaging session utilized fluorescein labeled antibody 16B5, a monoclonal directed against an intracellular epitope of human tau which does not cross react with rodent tau (Vigopelfry et al. *Neurology* 45:788-793 (1995), which is hereby incorporated by reference in its entirety). The initial imaging session, using antibody 16B5, did not image any amyloid-β at all, as expected, because the monoclonal antibody was not directed against an epitope present on senile plaques. Repeat imaging 3 to 5 days later using fluorescently labeled 10D5 imaged numerous amyloid-β deposits that were indistinguishable from the initial imaging sessions of any of the 6 mice initially imaged with 10D5. Thus, it does not appear that the surgical preparation, application of an irrelevant monoclonal antibody, or imaging per se led to resolution of amyloid-β deposits.

To explore the question of whether application of anti-amyloid-β antibodies altered both diffuse and compact, fibrillar deposits, an alternative imaging strategy was developed using thioflavine S. Thioflavine S is a standard fluorescent stain that specifically binds to amyloid protein deposits; it is commonly used in Alzheimer's Disease neuropathological studies. Application of a dilute solution (0.005% in ACSF) of thioflavine S (which fluoresces in the blue-green range) to the cortical surface at the same time as application of fluorescein labeled 10D5 or 16B5 allowed simultaneous observation of both dense cored thioflavine S positive plaques, and of all amyloid-β deposits. Nine animals were randomly assigned to a 10D5 (n=4, 7 sites) or 16B5 (n=5, 7 sites) treatment as above. Two independent readers scored the presence of thioflavine S plaques in each of 28 imaging sessions, and compared first and second imaging sets to determine whether individual thioflavine S plaques had been cleared. In the 10D5 group, 45 of 65 plaques (70%) were cleared 3 days after initial imaging. In the 16B5 group, only 9 of 45 plaques could not be re-identified 3 days later (20%) ($\chi^2$=30.5, p<0.001). This result demonstrates that both diffuse and fibrillar amyloid-β deposits are reversed by 10D5 application, and furthermore serves as a technical control showing that the lack of amyloid-β at the second imaging session is not due to antibody mediated alteration of the epitope, but to clearance of the deposits.

To further analyze the effects of imaging and of treatment with 10 D5, a histological study of the mice was performed after the second imaging session. Mice brains were fixed in 4% paraformaldehyde, cryoprotected in 15% glycerol, and sectioned at 40 microns on a freezing sledge microtome. Immunostaining with biotinylated or fluorescently tagged 3D6 showed an area, approximately 100-200 microns in depth from the surface of the skull opening, which showed markedly diminished amyloid-β deposits near the surface (FIG. 21) in all mice treated with 10D5, but in none of the sham treated mice as judged by an observer unaware of treatment status. Of note, 3D6 and 10D5 have adjacent but non-overlapping epitopes, and can double stain senile plaques regardless of the order in which they are applied. These results are consistent with the hypothesis that the amyloid-β deposits were cleared after initial treatment of the cortex with direct application of 10D5.

Histochemical staining with tomato lectin (Sigma), which detects microglial cells, revealed a marked upregulation of microglia at the site of imaging (FIG. 22), even in animals treated with 16B5. At most a modest astrocyte response was observed using immunostaining with anti-glial fibrillary acidic protein. These data suggest that clearance of amyloid-β after exposure to 10D5 is a specific response to anti-amyloid-β antibodies rather than a nonspecific response to injury.

The interaction between amyloid-β and microglia at the site of antibody application was next studied, because immunization with amyloid-β leads to an apparent ingestion of amyloid-β by microglia (Schenk et al. *Nature* 400:173-7 (1999), which is hereby incorporated by reference in its entirety). Using double immunofluorescence with fluorescein labeled tomato lectin and biotin labeled 3D6 (detected with avidin-cy3 (Jackson Inmunoresearch)), a marked microglial response completely surrounding the small amounts of remaining amyloid-β at the treatment site in the frontal/parietal cortex was observed (FIG. 23A). Distal to the site, e.g., in the temporal lobe, typical plaques had just a few associated microglia (FIG. 23B). Though activation of microglia occurred in both the treated and control animals near the imaging site, the association of microglia with amyloid-β deposits was dramatically different.

In summary, the above data show for the first time reversal of existing amyloid-β deposits in the brain due to an experimental intervention. There is a remarkable clearing of both diffuse and compact, thioflavine S stained amyloid-β deposits within 3 days of treatment with an anti-amyloid-β antibody by direct application to the cortex. The remaining amyloid-β appears to be surrounded by microglia. Parallel studies performed in an ex vivo system show that microglia are able to take up amyloid-β via Fc mediated phagocytosis, which leads to subsequent peptide degradation. Antibodies might also alter the fibrillogenesis of amyloid-β[13]. The current experiments also serve to confirm and extend the results of immunization with amyloid-β[3] because the current treatment was passive application of antibody. These data suggest that it is the humoral response that mediates the attenuation of amyloid-β deposition after immunization with amyloid-β, rather than necessarily a cellular immune response. As a result, these data support the idea that passive immunotherapy might be effective in preventing or clearing amyloid-β deposits in Alzheimer's Disease, an approach that would have the clinical advantages of being self-limited, of using a reagent designed to have optimal epitope characteristics, and of avoiding the need to obtain high titer immunization results in an elderly patient population.

A powerful in vivo multiphoton imaging technology is described that allows visualization of distinct brain lesions, in a living anesthetized mouse, with a resolution of approximately 1 micron. This provides extraordinary in vivo images of individual cells or pathological structures, with a resolution that far exceeds other in vivo technologies. In principle any extracellular epitope might be visualized with an appropriate direct labeled antibody. Antibody penetration into the cortex was not a limiting factor, and the antibody penetrated as deeply as the multiphoton microscope could detect—about 100 to 150 microns from the surface of the brain, or into layers II or III of the mouse cortex. Other fluorescent markers (either fluorescein or Texas red) reveal the vascular anatomy to provide landmarks, and would clearly be useful for studies directed at vascular pathology or amyloid angiopathy. A wide variety of fluorescent reporter molecules are available that could monitor metabolic and physiologic activity in vivo. Repeat imaging of the same site hours or days later can be readily obtained. Preliminary experience suggests that this time window can be extended to months with some modifications in the imaging protocols. The best imaging agent, fluorescently labeled 10D5, appears to have a striking therapeutic effect, but it is anticipated that modifications of this approach will yield valuable imaging agents that can be used to test other therapeutic approaches with in vivo multiphoton microscopy. The ability to image the same site longitudinally makes this imaging approach ideal for studies of diverse therapeutic interventions, and makes possible the unequivocal conclusion that treatment with anti-amyloid-β antibodies reverses amyloid-β deposits.

Neurofibrillary tangles are the other intracellular neuropathological hallmark of Alzheimer's Disease and occupy neurons in layer II, III, and V of the cortex. The primary protein that forms the neurofibrillary tangles is the microtubule-associated protein, tau, which self-aggregates in Aβ pleated sheet protein confirmation. This β-pleated sheet has the same type of structure as the amyloid-β protein in senile plaques, and hence, similar dyes bind to it. Thioflavin S also binds neurofibrillary tangles, as does congo red and any compounds that similarly bind amyloid. Fluorescent variants of these compounds, therefore, would be useful for in vivo detection of neurofibrillary tangles. Here, it has been demonstrated ex vivo that these compounds do stain tangles, and that they can be detected by multiphoton microscopy.

In addition, a second approach to detect neurofibrillary tangles is to take advantage of a unique autofluorescent signature of this protein structure.

FIG. 24A shows a typical neurofibrillary tangle, in a frozen sample of post-mortem human brain, imaged due to its unique autofluorescence properties when exposed to long wavelength light. To confirm its identity, immunohistochemistry with anti-phospho tau antibodies demonstrate the same cell. The unique emission spectrum of the tangle after exposure to light at 800 nanometers is illustrated in FIG. 24B.

The ability to diagnostically detect and image a neurodegenerative disease in animals using multiphoton excitation of brain tissue demonstrates the usefulness of multiphoton excitation to detect and image such disease in larger animals, including humans.

Although the invention has been described in detail for the purpose of illustration, it is understood that such details are solely for that purpose. The variations can be made therein by those skilled in the art without departing from the spirit of the scope of the invention which is defined by the following claims.

What is claimed is:

1. A method of detecting a neurodegenerative disease in a mammal comprising:
    activating brain tissue of the mammal by application of radiation from a laser through an opening or a thinned portion of the mammal's skull under conditions effective to promote a simultaneous multiphoton excitation of the brain tissue and to emit a fluorescence characteristic, wherein the radiation is at an intensity level capable of being achieved by a titanium sapphire mode locked solid state laser and has a wavelength in the visible red to the infrared region of the light spectrum and is pulsed at a pulse width between about $10^{-9}$ to $10^{-15}$ second, said fluorescence characteristic being achieved by combining photons;

comparing the fluorescence characteristic to a standard fluorescence emitted by exciting healthy brain tissue of the mammal under the same conditions used to carryout said activating; and identifying the brain tissue where the fluorescence characteristic differs from the standard fluorescence as potentially having a neurodegenerative disease.

2. The method according to claim 1 further comprising:
treating the brain tissue with at least one photo-active agent prior to said activating.

3. The method according to claim 2, wherein the standard fluorescence is determined prior to said treating the brain tissue with at least one photo-active agent.

4. The method according to claim 2, wherein the photo-active agent fluoresces upon binding to lesions of neurodegenerative disease or other neuroanomalies.

5. The method according to claim 1, wherein the laser is a mode-locked laser.

6. The method according to claim 1, further comprising:
collecting radiation applied to the brain tissue.

7. The method according to claim 1, wherein said identifying is carried out under conditions effective to determine whether the mammal has a neurodegenerative disease selected from the group consisting of Alzheimer's Disease, Parkinson's Disease, Huntington's Disease, and Lou Gehrig's Disease.

8. The method according to claim 7, wherein said identifying is carried out under conditions effective to determine whether the mammal has Alzheimer's Disease.

9. The method according to claim 8, wherein amyloid plaques are detected in the brain of the mammal.

10. The method according to claim 8, wherein neurofibrillary tangles are detected in the brain of the mammal.

11. The method according to claim 1, wherein the method is carried out in vivo.

12. The method according to claim 1, wherein the radiation is passed through a portion of the skull of the mammal which has been thinned.

13. The method according to claim 1, wherein the fluorescence characteristic is an autofluorescence characteristic.

14. The method according to claim 1, wherein the radiation has a wavelength of about 700 nm to about 1000 nm.

15. The method according to claim 1, wherein the radiation is applied through an opening of the mammal's skull.

16. A method of producing an image of brain tissue from a mammal comprising:

activating brain tissue of a mammal with radiation applied from a laser through an opening or a thinned portion of the mammal's skull under conditions effective to promote a simultaneous multiphoton excitation of the brain tissue and to produce a fluorescence, wherein the radiation is at an intensity level capable of being achieved by a titanium sapphire mode locked solid state laser and has a wavelength in the visible red to the infrared region of the light spectrum and is pulsed at a pulse width between about $10^{-9}$ to $10^{-15}$ second, said fluorescence being achieved by combining photons and collecting the fluorescence to produce an image of the brain tissue.

17. The method according to claim 16 further comprising:
treating the brain tissue with at least one photo-active agent prior to said activating.

18. The method according to claim 16, wherein the laser is a mode-locked laser.

19. The method according to claim 16, wherein the method is carried out on brain tissue affected with a neurodegenerative disease, whereby said collecting produces an image of the brain tissue affected with a neurodegenerative disease.

20. The method according to claim 19, wherein said collecting is carried out under conditions effective to produce an image of the brain tissue affected with a neurodegenerative disease selected from the group consisting of Alzheimer's Disease, Parkinson's Disease, Huntington's Disease, and Lou Gehrig's Disease.

21. The method according to claim 20, wherein said collecting is carried out under conditions effective to produce an image of the brain tissue affected with Alzheimer's Disease.

22. The method according to claim 21, wherein amyloid plaques are imaged in the brain of the mammal.

23. The method according to claim 21, wherein neurofibrillary tangles are detected in the brain of the mammal.

24. The method according to claim 16, wherein the method is carried out in vivo.

25. The method according to claim 16, wherein the radiation is passed through a portion of the skull of the mammal which has been thinned.

26. The method according to claim 16, wherein the fluorescence is autofluorescence.

27. The method according to claim 16, wherein the radiation has a wavelength of about 700 nm to about 1000 nm.

28. The method according to claim 16, wherein the radiation is applied through an opening of the mammal's skull.

* * * * *